United States Patent
Hamilton et al.

(10) Patent No.: US 7,963,916 B2
(45) Date of Patent: Jun. 21, 2011

(54) METHOD AND APPARATUS FOR ESTIMATING A LIKELIHOOD OF SHOULDER DYSTOCIA

(75) Inventors: Emily Hamilton, Verdun (CA); Christa D. Fairchild, Verdun (CA); Isabelle Lafortune, Hampstead (CA)

(73) Assignee: Perigen, Inc., Princeton, NJ (US)

( * ) Notice: Subject to any disclaimer, the term of this patent is extended or adjusted under 35 U.S.C. 154(b) by 1466 days.

(21) Appl. No.: 11/262,425

(22) Filed: Oct. 28, 2005

(65) Prior Publication Data
US 2006/0116560 A1    Jun. 1, 2006

Related U.S. Application Data

(63) Continuation-in-part of application No. 10/999,715, filed on Nov. 30, 2004.

(51) Int. Cl.
*A61B 5/00* (2006.01)
(52) U.S. Cl. ............... 600/300; 128/920; 702/19
(58) Field of Classification Search .......... 600/301, 600/300
See application file for complete search history.

(56) References Cited

U.S. PATENT DOCUMENTS

| | | | |
|---|---|---|---|
| 6,026,526 | A | 2/2000 | Payman |
| 6,322,504 | B1 | 11/2001 | Kirshner |
| 6,522,098 | B1 | 2/2003 | Majumdar et al. |
| 6,620,171 | B2 | 9/2003 | Vines |
| 6,684,165 | B2 | 1/2004 | Peisner |
| 6,690,958 | B1 | 2/2004 | Walker et al. |
| 6,695,780 | B1 * | 2/2004 | Nahum et al. ............ 600/437 |
| 2003/0018520 | A1 * | 1/2003 | Rosen ...................... 705/12 |

FOREIGN PATENT DOCUMENTS
WO    2004/110262    12/2004

OTHER PUBLICATIONS

Langer et al. "Shoulder dystocia: should the fetus weighing >= 4000 grams be delivered by caesarian section?". American Journal of Obstetrics and Gynecology. 1991. abstract only.*
Pearson, James F. "Shoulder dystocia." Current Obstetrics & Gynecology. vol. 6, Issue 1, Mar. 1996, pp. 30-34. abstract only.*
Geary, Michael et al. "Shoulder Dystocia—Is It Predictable?" *European Journal of Obstetrics & Gynecology and Reproductive Biology* (1995) vol. 62, No. 1, pp. 15-18, XP 002354347.
Wolfe, Honor et al. "The Clinical Utility of Maternal Body Mass Index in Pregnancy" *American Journal of Obstetrics and Gynecology* (1991) vol. 164, No. 5, pp. 1306-1310, XP 009057068.

(Continued)

*Primary Examiner* — Patricia C Mallari
(74) *Attorney, Agent, or Firm* — Ladas & Parry LLP

(57) ABSTRACT

A system and apparatus implementing a graphical user interface module for displaying information conveying a level of risk of delivery with shoulder dystocia associated to an obstetrics patient. The graphical user interface module displays a set of user modifiable information fields for allowing a user to enter a set of patient information data elements associated to the obstetrics patient. The graphical user interface module also displays a control allowing a user to cause the set of information data elements to be transmitted to a processing unit adapted to derive patient risk data at least in part on the basis of the set of information data elements, the patient risk data conveying a level of risk of delivery with shoulder dystocia. The graphical user interface module then displays the patient risk data with reference to risk assessment information.

45 Claims, 21 Drawing Sheets

OTHER PUBLICATIONS

Mehta, S., et al. "Maternal Body Mass Index and Fetal Weight in Shoulder Dystocia." SMFM Abstracts, American Journal of Obstetrics and Gynecology (2003).

Rouse, DJ., et al. "The Effectiveness and Costs of Elective Cesarean Delivery for Fetal Macrosomia Diagnosed by Ultrasound." JAMA (1996) vol. 276, No. 18, pp. 1480-1486.

Gherman, RB. "Shoulder Dystocia: An Evidence-Based Evaluation of the Obstetric Nightmare." Clinical Obstetrics and Gynecology (2002) vol. 45, No. 2, pp. 345-362.

ACOG Practice Bulletin: "Shoulder Dystocia." No. 40 (2002) (Replaces practice pattern No. 7, Oct. 1997).

Baskett, T. "Shoulder Dystocia." Best Practice & Research Clinical Obstetrics and Gynaecology (2002) vol. 16, No. 1, pp. 57-68.

Zylstra, S., et al. "Cutting the Medicolegal Risk of Shoulder Dystocia." OBG Management (2004), pp. 78-98.

Gudmundsson, S., et al. "Correlation of birth injury with maternal height and birthweight." BJOG: An International Journal of Obstetrics and Gynaecology 111 (2004), pp. 1-4.

Hope, P., et al. "Fatal shoulder dystocia: A review of 56 cases reported . . ."British Journal of Obstetrics and Gynaecology, vol. 105 (1998) pp. 1256-1261.

Office Action Mailed on Jul. 11, 2008 in Connection With U.S. Appl. No. 10/999,715, 12 Pages.

Office Action Mailed on Apr. 15, 2009 in Connection With U.S. Appl. No. 10/999,715, 13 Pages.

Partial European Search Report Completed on Nov. 16, 2005 in Connection With EP Patent Application No. 05 10 6762, 4 Pages.

Office Action Dated Jan. 2, 2007 in Connection With EP Patent Application No. 05 10 6752, 5 Pages.

Office Action dated May 18, 2010 in connection with U.S. Appl. No. 10/999,715, 17 pages.

Jolly, et al., "Risk factors for macrosomia and its clinical consequences: A study of 350,311 pregnancies", European Journal of Obstetrics & Gynecology and Reproductive Biology 111 (2003), pp. 9-14.

Van Wootten et al., "The prevalence of macrosomia in neonates of gestational diabetic mothers: analysis of risk factors", Sep. 1999, abstract only, 1 page.

Pearson, James F., "Shoulder dystocia", Current Obsterics & Gynecology, vol. 6, issue 1, Mar. 1996, abstract only, pp. 30-34.

Langer et al., "Shoulder dystocia: should the fetus weighing >=4000 grams be delivered by caesarian section?", American Journal of Obstetrics and Gynecology, 1991, abstract only, 4 pages.

Office Action of Feb. 17, 2011 in European Patent Application No. 05106762.7.

* cited by examiner

RISK OF SHOULDER DYSLOCIA ANALYSIS

PRE LABOR FACTORS
- MATERNAL WEIGHT – 165
- MATERNAL HEIGHT – 160
- EXPECTED FETAL WEIGHT – 4200g - 4500g  ⎯502

LABOR FACTORS
- N/A  ⎯504

RANKING
- 8/10 TO 9/10  ⎯506

RECOMMENDATIONS
- At this ranking, intervention in the form of a cesarean section is moderately to highly recommended  ⎯508

FIG. 5

Shoulder Dystocia Screening

⊙start here

| | | |
|---|---|---|
| Is this the mother's first vaginal birth? | ○Yes ●No ←1704 | |
| Maternal diabetes | ○Yes ●No ←1706 | |
| Mother's weight | 154  ○kg ●lbs ←1708 | |
| Gestational age | 41 wks  0 days ←1710 | |
| Mother's height | 5'/6"  ○meters ●feet. inches ←1712 | 1702 |
| Estimated fetal weight | 4,300  ●grams ○lbs. oz. ←1714 | |
| Lower estimated weight value* | 3,900  ●grams ○lbs. oz. | 1719 |
| Higher estimated weight value* 1750 | 4,700  ●grams ○lbs. oz. | |

*Required fields.  1762   1718—  (clear)
⊙) CALCULATE NOW   1722 results ❓

1724 — low risk | high risk

Shoulder screen status
The values indicate a score of 0.05 (range 0.02 to 0.11) which is below the threshold established.
Click ❓ for more information.   1726
1780—

1720  0  0.05  0.1  0.15  0.2  0.25  0.3  0.35  0.4  0.45  0.5  0.55  0.6  0.65

View references
- ● ○ Add reference range for women with vaginal delivery without shoulder dystocia  1730
- ● ○ Add reference range for women with shoulder dystocia and injury  1732
- ● ○ Add selected threshold  1734

% of Mothers: 80%, 70%, 60%, 50%, 40%, 30%, 20%, 10%, 0%
low risk | high risk
1736  1740  1728

0  0.05  0.1  0.15  0.2  0.25  0.3  0.35  0.4  0.45  0.5  0.55  0.6  0.65 comments   1760
1738—   1752  1754  1756
(save) (print) (clear)

FIG. 17A

Shoulder Dystocia Screening

⊙start here

| | | |
|---|---|---|
| Is this the mother's first vaginal birth? | ○Yes ●No ←—1704 | |
| Maternal diabetes | ○Yes ●No ←—1706 | |
| Mother's weight | 154 ○kg ●lbs ←—1708 | |
| Gestational age | 41 wks 0 days ←—1710 | |
| Mother's height | 5'/6" ○meters ●feet. inches ←—1712 | 1702 |
| Estimated fetal weight | 4,300 ●grams ○lbs. oz. ←—1714 | |
| Lower estimated weight value* | 3,900 ●grams ○lbs. oz. ←—1719 | |
| Higher estimated weight value*  1750 | 4,700 ●grams ○lbs. oz. | |

*Required fields.

1718 — ( clear )

1762  ⊙》 CALCULATE NOW   1722 results ❓

1724 — low risk | high risk

Shoulder screen status
The values indicate a score of 0.05 (range 0.02 to 0.11) which is below the threshold established. Click ❓ for more information.

1726
1780

1720  0  0.05  0.1  0.15 | 0.2  0.25  0.3  0.35  0.4  0.45  0.5  0.55  0.6  0.65

80%
70%  low risk | high risk
60%
50%             1730
40%             1732
% of Mothers
30%    1740   1734
20%
10%
0%
0  0.05  0.1  0.15  0.2  0.25  0.3  0.35  0.4  0.45  0.5  0.55  0.6  0.65

View references
○—○ Add reference range for women with vaginal delivery without shoulder dystocia
●—○ Add reference range for women with shoulder dystocia and injury
●—○ Add selected threshold

1728 comments
1760
1752  1754  1756
1738
( save )( print )( clear )

FIG. 17B

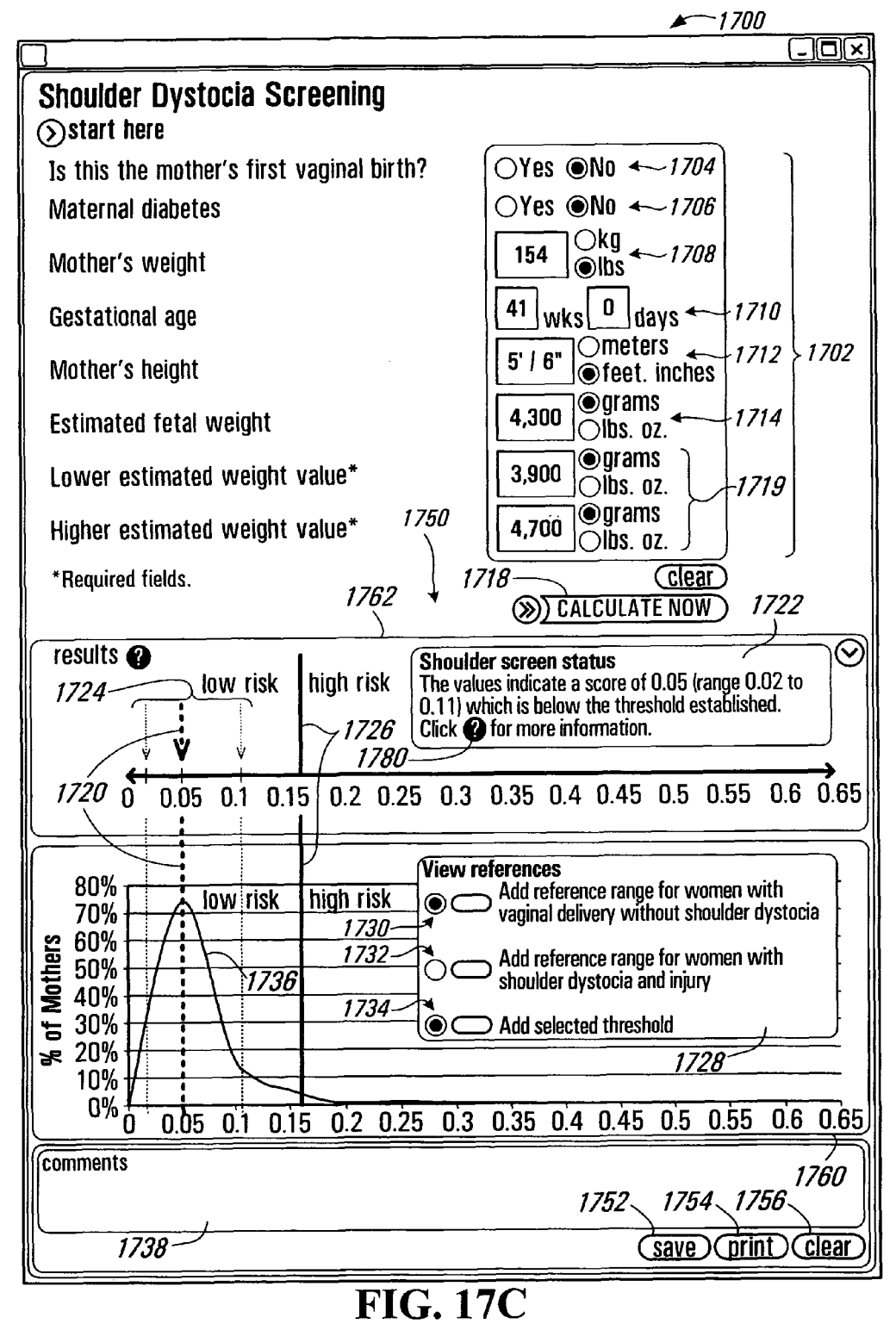

Shoulder Dystocia Screening

⊙ start here

| | | |
|---|---|---|
| Is this the mother's first vaginal birth? | ○Yes ●No ←—1704 | |
| Maternal diabetes | ○Yes ●No ←—1706 | |
| Mother's weight | [154] ○kg ●lbs ←—1708 | |
| Gestational age | [41] wks [0] days ←—1710 | |
| Mother's height | [5'/6"] ○meters ●feet.inches ←—1712 | 1702 |
| Estimated fetal weight | [4,300] ●grams ○lbs. oz. ←—1714 | |
| Lower estimated weight value* | [3,900] ●grams ○lbs. oz. | 1719 |
| Higher estimated weight value* | [4,700] ●grams ○lbs. oz. | |

1750

*Required fields.

1762    1718 — (clear)
        (>>) CALCULATE NOW    1722 results ❓

1724 — low risk | high risk    Shoulder screen status
                                The values indicate a score of 0.05 (range 0.02 to
                         1726   0.11) which is below the threshold established.
                                Click ❓ for more information.
                         1780

1720  0  0.05  0.1  0.15 | 0.2  0.25  0.3  0.35  0.4  0.45  0.5  0.55  0.6  0.65

View references

80% —
70% — low risk | high risk    ● ○ Add reference range for women with
60% —                               vaginal delivery without shoulder dystocia
% of Mothers 50% —  1730 —
40% —          1732 —         ○ ○ Add reference range for women with
30% —    1736  1734 —               shoulder dystocia and injury
20% —
10% —                         ● ○ Add selected threshold
0%                                                              1728
    0  0.05  0.1  0.15  0.2  0.25  0.3  0.35  0.4  0.45  0.5  0.55  0.6  0.65 comments
                                                                    1760
                                                   1752  1754  1756
1738                                               (save)(print)(clear)

FIG. 17C

Shoulder Dystocia Screening

> start here

| | | |
|---|---|---|
| Is this the mother's first vaginal birth? | ○Yes ●No ←―1704 | |
| Maternal diabetes | ○Yes ●No ←―1706 | |
| Mother's weight | 154 ○kg ●lbs ←―1708 | |
| Gestational age | 41 wks 0 days ←―1710 | 1702 |
| Mother's height | 5'/6" ○meters ●feet. inches ←―1712 | |
| Estimated fetal weight | 4,300 ●grams ○lbs. oz. ←―1714 | |
| Lower estimated weight value* | 3,900 ●grams ○lbs. oz. ―1719 | |
| Higher estimated weight value* | 4,700 ●grams ○lbs. oz. | |

*Required fields.

1718 — clear
>> CALCULATE NOW   1722 results ❓

1724 — low risk | high risk

Shoulder screen status
The values indicate a score of 0.05 (range 0.02 to 0.11) which is below the threshold established.
Click ❓ for more information.

1720  0  0.05  0.1  0.15  0.2  0.25  0.3  0.35  0.4  0.45  0.5  0.55  0.6  0.65

% of Mothers (80%-0%)  low risk | high risk 0  0.05  0.1  0.15  0.2  0.25  0.3  0.35  0.4  0.45  0.5  0.55  0.6  0.65

View references
○⬭ Add reference range for women with vaginal delivery without shoulder dystocia — 1730
○⬭ Add reference range for women with shoulder dystocia and injury — 1732
●⬭ Add selected threshold — 1734

1728 comments
1760
1752  1754  1756
1738    save  print  clear

Number ID
Shoulder dystocia ○Yes ○No          Spont vag delivery ○          Cesarean ○
Date of Delivery                                    Forceps ○
                                                    Vacuum ○

First vaginal birth ○Yes ○No     Time of start of 2$^{nd}$ Stage       Last Maternal Height
Diabetes ○Yes ○No                Time of delivery of head              Last Maternal Weight
Previous SD ○Yes ○No             Time delivery completed               Birth Weight
Gestational age

Delivery techniques                Shoulder Description              Measurements

Episiotomy No 2$^{nd}$ 3$^{rd}$ 4$^{th}$                                     Date of Last US
McRobert's ○Yes ○No              Anterior arm ○R L○                    EFW on last US
Shoulder rotation ○Yes ○No       Neonatal injury ○Yes ○No              EFW on admission
(Wood's or Rubin)
Posterior arm ○Yes ○No           Erb's palsy ○Yes ○No                  Apgar 1, 5,10       artery    vein
Fundal pressure ○Yes ○No         Clavicular fracture ○Yes ○No          Cord gases
Head pushed back ○Yes ○No        Humeral fracture ○Yes ○No                    pH
                                 Seizures ○Yes ○No                            PCO$_2$
                                 Death ○Yes ○No                               PO$_2$
                                                                       Base deficit
                                 Chart documentation1
Level of traction                Other description 2                   Moro reflex ○Symmetric ○Asymmetric
Other technique                                                        Other 1
                                                                       Other 2

Comments

METHOD AND APPARATUS FOR ESTIMATING A LIKELIHOOD OF SHOULDER DYSTOCIA

CROSS-REFERENCE TO RELATED APPLICATIONS

This application is a continuation-in-part application of U.S. patent application Ser. No. 10/999,715 filed Nov. 30, 2004. The contents of the above referenced application are incorporated herein by reference.

FIELD OF THE INVENTION

The present invention relates generally to the field of obstetrics, and more specifically to a method and apparatus for estimating a likelihood of shoulder dystocia and for providing a user interface to display information conveying a level of risk of delivery with shoulder dystocia associated to an obstetrics patient.

BACKGROUND OF THE INVENTION

Shoulder dystocia (SD) refers to excessive difficulty in delivering the baby vaginally after the head is born because of the position or diameter of the shoulders. The reported incidence of shoulder dystocia varies from 0.6% to 1.4% among vaginal deliveries. When the baby's head is born and the shoulders are trapped within the birth canal, the baby's chest is compressed within the birth canal preventing it from breathing and the umbilical cord is compressed reducing the amount of oxygen supplied to the baby. Special delivery procedures are recommended to ease the passage of the shoulders and allow the baby to be completely born without undue delay or force. During such a birth, the nerves in the baby's neck, leading to the arm (the brachial plexus), can be stretched and injured. Neonatal injuries associated with shoulder dystocia include brachial plexus injury in 4 to 40%, clavicular fracture in 5.1 to 7.5% and very rarely brain damage or death. Although most brachial plexus injuries will recover, those that do not may result in permanent weakness or paralysis in the arm. Reported rates of persistent palsy range from 3 to 50% (ACOG Technical Bulletin Number 40, 2002, Baskett T F, 2002, Gherman R B, 2002). Injury from shoulder dystocia is a common cause of litigation and failure to adequately predict and or communicate the risk of shoulder dystocia and injury is commonly alleged in legal actions.

If the likelihood of shoulder dystocia with neonatal injury for a given obstetrics patient could be accurately estimated, it would desirable to intervene when the likelihood of shoulder dystocia is high such as to avoid (or at least reduce the rate of) neonatal injuries caused by this situation. Intervention may be in the form of elective cesarean delivery for example.

For the reader's information, the following are a few studies related to shoulder dystocia:

1. ACOG practice bulletin: Shoulder dystocia. Number 40, November 2002. (Replaces practice pattern number 7, October 1997).
2. Baskett T F. Shoulder Dystocia. Best Practice & Research Clinical Obstetrics and Gynecology 2002; 16:57-68.
3. Rouse D J, Owen J, Goldenberg R L, Cliver S P. The Effectiveness and Costs of Elective Cesarean Delivery for Fetal Macrosomia diagnosed by Ultrasound. JAMA. 1996; 276(18): 1480-6.
4. Gherman R B. Shoulder Dystocia: An Evidence-Based Evaluation of the Obstetric Nightmare. Clinical Obstetrics and Gynecology 2002; 45:345-362.

The contents of the above documents are herein incorporated by reference.

Generally, professional societies recommend intervention based on a hard threshold of estimated fetal weight, which may be modified by the presence or absence of diabetes, or recommend making a qualitative judgment about risk factors in general. Large fetal weight is generally considered as being the most consistent and important factor in predicting an increase in the risk of shoulder dystocia (SD). For that reason, some professional societies recommend elective cesarean if the fetal weight is estimated to be over 5000 g in women without diabetes and 4500 g in women with diabetes. Other studies could not justify intervention at the 4500 gram estimated weight threshold even in the presence of gestational diabetes.

A deficiency associated with existing methods, such as the ones described in the above noted publications, is that in order to detect a high percentage of babies with the relatively rare condition of shoulder dystocia, an unacceptable rate of false positive predictions occurs in the more common uncomplicated pregnancies. This could lead to excessive numbers of unnecessary interventions in women rendering the prediction of little clinical value. For example, it has been estimated that by having a policy of intervention at 4500 gram, an extra 443 cesareans would be required to avoid a single case of permanent brachial palsy injury. The financial cost of such a policy would be about $930,000US for each avoided case of permanent brachial palsy injury without counting the emotional and physical trauma of the 443 mothers who underwent essentially unnecessary cesareans. (Rouse D J et al 1996—reference 3 above) Moreover, several studies have shown that a substantial number of cases of shoulder dystocia occurs in women with infants weighing less than 4000 g. Therefore, even though fetal weight is an important factor in predicting shoulder dystocia, it is nevertheless not sufficiently reliable and does not provide a suitable prediction of the level of risk shoulder dystocia for an individual mother. In fact, the ACOG Practice bulletin (reference 1 above) concludes, "Shoulder dystocia is most often unpredictable and unpreventable".

Another deficiency is that there are no suitable tools for providing the clinical staff with an indication of the level of risk of delivery with shoulder dystocia associated to an obstetrics patient.

Therefore, in the context of the above, there is a need to provide a method and apparatus for estimating a level of risk of shoulder dystocia associated to an obstetrics patient that alleviates at least in part problems associated with the existing methods and devices.

SUMMARY OF THE INVENTION

In accordance with a broad aspect, the invention provides a computer readable storage medium storing a program element suitable for execution by a CPU. The program element implements a graphical user interface module for displaying information conveying a level of risk of delivery with shoulder dystocia associated to an obstetrics patient. The graphical user interface module is adapted for displaying a set of user modifiable information fields for allowing a user to enter a set of patient information data elements associated to the obstetrics patient. The graphical user interface module is also adapted for displaying a control allowing a user to cause the set of information data elements to be transmitted to a processing unit. The processing unit is adapted to derive patient risk data at least in part on the basis of the set of information data elements, the patient risk data conveying a level of risk of delivery with shoulder dystocia. The graphical user interface module receives patient risk data and is adapted to display the patient risk data with reference to risk assessment information.

In accordance with a specific implementation, the set of patient information data elements comprises a maternal weight component, a maternal height component and a fetal weight component. Optionally, the set of patient information data elements may further include a previous vaginal birth indicator component, a maternal diabetes indicator component, gestational age component and any other suitable item of information associated to the obstetrics patient.

In accordance with a specific implementation, the patient risk data includes a ranking data element conveying a level of risk of delivery with shoulder dystocia associated to the obstetrics patient. The ranking data element may be expressed in the form of a score, a likelihood, a risk level selected from a set of risk levels, as a percentile value or in any other format suitable for conveying a relative level of risk.

In accordance with a specific implementation, the control allows the user to cause the set of information data elements to be transmitted to a processing unit by using an input device selected from the set consisting of a mouse, keyboard, pointing device, speech recognition unit and touch sensitive screen.

The risk assessment information may be conveyed in any suitable format including graphical and textual formats. In accordance with a specific implementation, the risk assessment information conveys a first reference range of levels of risk associated to women who delivered without shoulder dystocia. Optionally, the risk assessment information further conveys a second reference range of levels of risk associated to women who delivered with shoulder dystocia. Optionally still, the risk assessment information further conveys a threshold level of risk. In accordance with a non-limiting implementation, the risk assessment data further conveys at least one recommendation data element associated to the obstetrics patient.

In accordance with a specific implementation, the graphical user interface module is adapted for displaying a graph conveying risk assessment information including:
   first information indicative of a reference range of levels of risk associated to women who delivered with shoulder dystocia;
   second information indicative of a reference range of levels of risk associated to women who delivered without shoulder dystocia; and
   third information conveying a threshold level of risk of delivery with shoulder dystocia.

In accordance with a specific implementation, the control on the graphical user interface module is a first control and the graphical user interface module is adapted for displaying a second control. The second control is for allowing a user to cause the first information to be removed from the graph conveying risk assessment information. Optionally, the graphical user interface module is adapted for displaying a third control allowing a user to cause the second information to be removed from the graph conveying risk assessment information. Optionally still, the graphical user interface module is adapted for displaying a fourth control allowing a user to cause the third information to be removed from the graph conveying risk assessment information.

In accordance with another broad aspect, the invention provides an apparatus for implementing a user interface for displaying information conveying a level of risk of delivery with shoulder dystocia associated to an obstetrics patient. The apparatus comprises an input for receiving a set of patient information data elements associated to the obstetrics patient, a processing unit coupled to the input and an output coupled to the processing unit. The processing unit is operative for implementing a graphical user interface module for displaying information conveying a level of risk of delivery with shoulder dystocia associated to an obstetrics patient. The graphical user interface module is adapted for displaying a set of user modifiable information fields for allowing a user to enter a set of patient information data elements associated to the obstetrics patient. The graphical user interface module is also adapted for displaying a control allowing a user to cause the set of information data elements to be processed to derive patient risk data at least in part on the basis of the set of information data elements. The patient risk data conveys a level of risk of delivery with shoulder dystocia. The graphical user interface module is also adapted for displaying the patient risk data with reference to risk assessment information. The output is coupled to the processing unit and is suitable for releasing a signal for causing a display unit to display the graphical user interface module.

In accordance with a specific implementation, the set of patient information data elements comprises a maternal weight component, a maternal height component and a fetal weight component. Optionally, the set of patient information data elements may further include a previous vaginal birth indicator component, a maternal diabetes indicator component, gestational age component and any other suitable item of information associated to the obstetrics patient.

In accordance with another broad aspect, the invention provides a method suitable to be implemented on a general purpose computing unit for displaying information conveying a level of risk of delivery with shoulder dystocia associated to an obstetrics patient. The method comprises displaying a set of user modifiable information fields for allowing a user to provide a set of patient information data elements associated to the obstetrics patient. The method also includes displaying a control allowing a user to cause the set of information data elements to be transmitted to a processing unit, the processing unit being adapted to derive patient risk data at least in part on the basis of the set of information data elements. The patient risk data conveys a level of risk of delivery with shoulder dystocia. The method also includes displaying the patient risk data with reference to risk assessment information.

In accordance with another broad aspect, the invention provides a method for estimating a level of risk of shoulder dystocia associated to an obstetrics patient. The method comprises receiving a set of information data elements associated to an obstetrics patient, the set of information data elements including information derived from a maternal weight component, a maternal height component and a fetal weight component. The method also includes transmitting the set of information data elements to a processing unit adapted to derive a ranking data element associated to the obstetrics patient, the ranking data element conveying a level of risk of delivery with shoulder dystocia. The method also comprises receiving a signal conveying the ranking data element and causing the ranking data element to be displayed to a user with reference to risk assessment information to convey a level of risk of delivery with shoulder dystocia.

The ranking data element may be represented in any suitable format. In a specific example of implementation, the ranking data element is indicative of a likelihood score. In an alternative example of implementation, the ranking data element is indicative of a risk level selected from a set of risk levels.

In a specific example of implementation, the method further comprises receiving a signal conveying at least one recommendation data element associated to the obstetrics patient.

In accordance with yet another broad aspect, the invention provides an apparatus for implementing a user interface for displaying information conveying a level of risk of delivery with shoulder dystocia associated to an obstetrics patient. The apparatus comprises means for receiving a set of patient information data elements associated to the obstetrics patient. The apparatus also comprises means for implementing a graphical user interface module for displaying information conveying a level of risk of delivery with shoulder dystocia associated to an obstetrics patient. The graphical user interface module is adapted for displaying a set of user modifiable information fields for allowing a user to enter a set of patient information data elements associated to the obstetrics patient. The graphical user interface module is also adapted for displaying a control allowing a user to cause the set of information data elements to be processed to derive patient risk data at least in part on the basis of the set of information data elements. The patient risk data conveys a level of risk of delivery with shoulder dystocia. The graphical user interface module is also adapted for displaying the patient risk data with reference to risk assessment information. The apparatus also includes means for releasing a signal for causing a display unit to display the graphical user interface module.

These and other aspects and features of the present invention will now become apparent to those of ordinary skill in the art upon review of the following description of specific embodiments of the invention in conjunction with the accompanying drawings.

BRIEF DESCRIPTION OF THE DRAWINGS

In the accompanying drawings:

FIG. 5 shows a first non-limiting example of a visual representation of the data released by the processing unit shown in FIG. 1 in accordance with a specific example of implementation of the present invention;

FIGS. 17a, 17b, 17c and 17d show specific examples of implementation of a graphical user interface for providing information conveying a level of risk of delivery with shoulder dystocia associated to an obstetrics patient in accordance with a non-limiting example of implementation of the invention;

FIG. 20 shows a specific example of implementation of user interface for allowing a health care practitioner to provide outcome information in accordance with a non-limiting example of implementation of the invention.

Other aspects and features of the present invention will become apparent to those ordinarily skilled in the art upon review of the following description of specific embodiments of the invention in conjunction with the accompanying figures.

DETAILED DESCRIPTION

The present detailed description describes a method and apparatus and system directed to estimating a level of risk of shoulder dystocia associated to an obstetrics patient. The expression shoulder dystocia is used to refer to either one or both the incidence of shoulder dystocia with neonatal injury and shoulder dystocia without neonatal injury. It will however be appreciated that shoulder dystocia with neonatal injury is considered more desirable to predict. Consequently, the specific embodiments of the invention described herein are used to estimate a level of risk of shoulder dystocia with neonatal injury. However, alternative embodiments of the invention may be implemented to estimate a level of risk of shoulder dystocia without neonatal injury and such alternative embodiments fall within the scope of the present invention.

In biomechanical terms shoulder dystocia is a misfit between the bisacromial diameter of the baby's shoulders and the anteroposterior diameter of the mother's pelvis. Factors associated with a large shoulder diameter include a high birth weight, maternal diabetes, and later gestational age. Factors associated with smaller pelvic diameters include small or short mothers and maternal obesity. These factors can be estimated prior to labour. Other factors that are known later, such as slow labour and the need for instrumental vaginal delivery, may be functional reflections of a potential misfit. The system described herein below makes use of a multifactorial mathematical predictive model using some of these factors in order to provide an estimate of risk of shoulder dystocia with neonatal injury.

Figure 1:
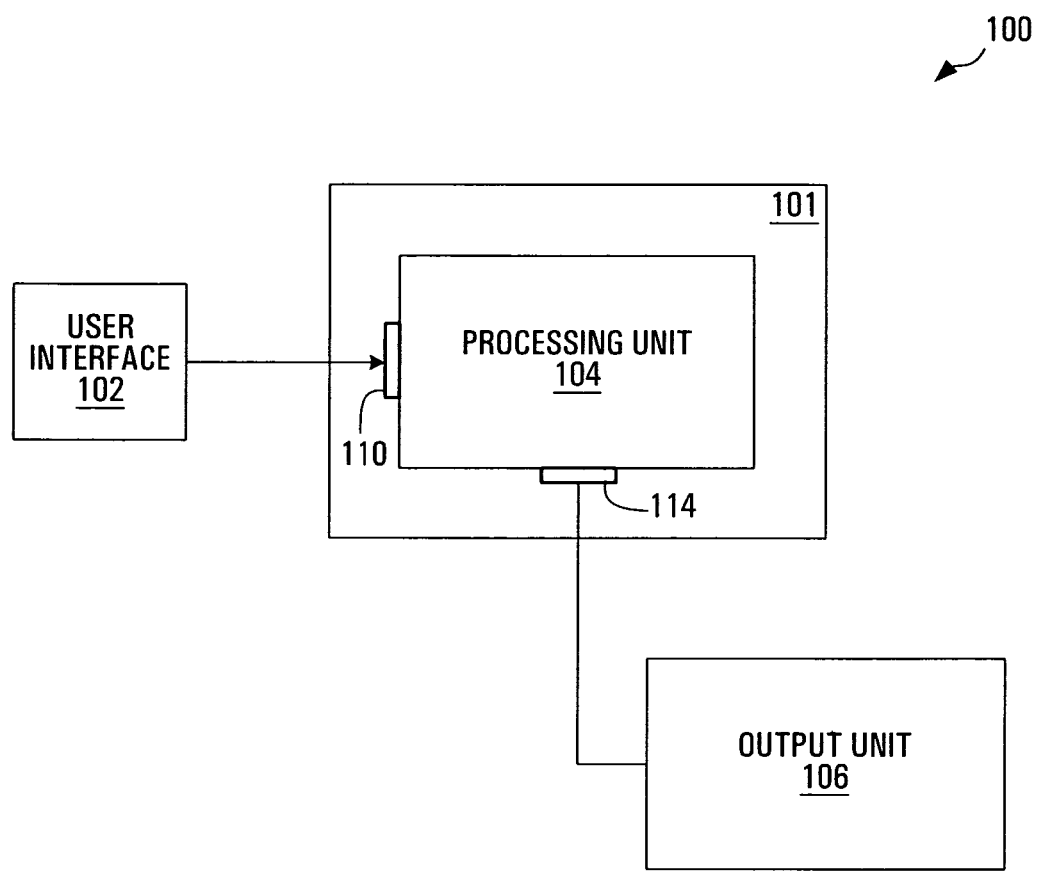
FIG. 1 shows a high-level functional block diagram of a system for estimating a level of risk of shoulder dystocia associated to an obstetrics patient in accordance with a specific example of implementation of the present invention.

With reference to FIG. 1, there is shown a configuration of a system 100 for estimating a level of risk of shoulder dystocia associated to an obstetrics patient. The system 100 may be used prior to labour onset (during late pregnancy) or during labour to estimate a level of risk of shoulder dystocia. Although, in theory, the system may be used at any time during labour prior to delivery, convenient times for using the system include at labour onset (very early in labour), at the end of the first stage of labour and prior to use of an instrumental vaginal delivery. Optionally, the system 100 can be used prior to labour onset or at the beginning of labour and then again at certain points throughout the labour as information about the labour progression becomes available. The level of risk of shoulder dystocia may be used, alone or in combination with a hospital policy, to assist a physician in determining whether an intervention is advisable.

As shown in FIG. 1, the system 100 comprises a user interface 102, an apparatus 101 including a processing unit 104, and an output unit 106.

The user interface 102 includes any one or a combination of a keyboard, a pointing device, a touch sensitive surface, a speech recognition unit or any other suitable device. Alternatively, the user interface 102 may be in the form of a data input device such as, but not limited to, a disk drive, CD-ROM and flash memory. The user interface 102 enables a user to provide a set of information data elements associated to a certain obstetrics patient.

Figure 3:
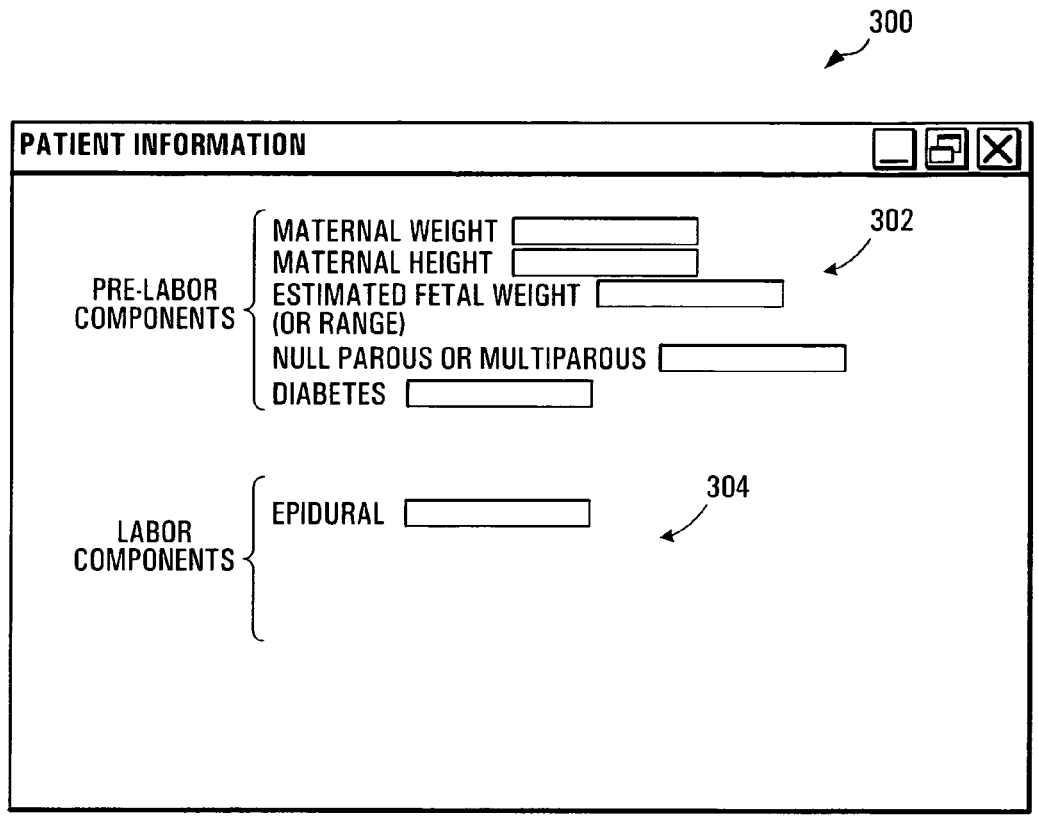
FIG. 3 shows a set of information data elements associated to an obstetrics patient in accordance with a non-limiting example of implementation of the present invention for use in the apparatus shown in FIG. 1.

FIG. 3 of the drawings depicts a non-limiting example of a set of information data elements associated to a certain obstetrics patient. In the specific example depicted, the set of information data elements 300 includes pre-labour components 302 and labour components 304. It will be apparent that where the system is used prior to labour onset, labour components 304 are omitted from the set of information data elements. In a specific example of implementation, the set of information data elements includes information derived from a maternal weight component, a maternal height component and a fetal weight component. In a specific implementation, the set of information elements includes a maternal Body Mass Index (BMI). The maternal BMI is derived on the basis of a maternal weight component and a maternal height component in accordance with well-know methods. It will be appreciated that, prior to delivery, the actual fetal weight is not known. Consequently, the fetal weight component may be an estimated fetal weight or an estimated range of fetal weights. Any suitable method for obtaining an estimate of a fetal weight (or range of fetal weights) for a fetus in utero may be used. Such methods are well known in the art of obstetrics and as such will not be described further here. Optionally, the set of information data elements also includes, without being limited to, information derived from a maternal age component, a maternal diabetes indicator, gestational age, a previous vaginal birth indicator (nulliparous or multiparous patient) and shoulder dystocia in previous pregnancies. Optionally still, when the system is used subsequent to labour onset, the set of information data elements may include information derived from labour information elements. Examples of labour information elements include, without being limited to, induction of labour, epidural anesthesia, length of the first labour stage, the length of the labour second stage and intended operative vaginal delivery. Other suitable information data elements may also be provided through user interface 102 without detracting from the spirit of the invention.

In the specific embodiment shown in FIG. 1, apparatus 101 includes a processing unit 104, an input 110 and an output 114. Input 110 is operative for receiving signals from the user interface 102 indicative of a set of information data elements associated to the obstetrics patient.

As shown in FIG. 1, the processing unit 104 is in communication with input 110 for receiving the signal or signals indicative of a set of information data elements associated to the obstetrics patient. As will be described in more detail below, on the basis of the signal or signals received at input 110, the processing unit 104 is operative to generate a ranking data element conveying a level of risk of shoulder dystocia associated to the obstetrics patient. The ranking data element is generated at least in part on the basis of a predictive model, which combines the set of information data elements associated to the obstetrics patient. Various predictive models may be used here. In a specific implementation, the predictive model includes a combination of a maternal height and weight and a fetal weight. In a non-limiting implementation the predictive model computes a score including a factor having the form BMI×fetal weight where BMI denotes a maternal body mass index. The manner in which suitable predictive models may be generated is described later on in the specification.

The ranking data element may be expressed in the form of a score, a likelihood, a risk level selected from a set of risk levels, as a percentile value or in any other format suitable for conveying a level of risk. The following table illustrates a limited number of formats for expressing a ranking data element. It will be appreciated that the ranking data element may be expressed in other suitable formats without detracting from the spirit of the invention.

| Sample Formats for Ranking Data Elements | | | |
| --- | --- | --- | --- |
| Likelihood | Classification | Score | Colour Scheme |
| .10 | Low risk | 100 | Green |
| .25 | Medium risk | 150 | Yellow |
| .5 | High risk | 190 | Orange |
| .8 | Very high risk | 225 | Red |

In a specific implementation where the set of information data element associated to the obstetrics patients includes a fetal weight component in the form of a range of fetal weights, the processing unit 104 is operative for generating a range of ranking data elements associated to the range of fetal weights. More specifically, ranking data elements can be derived using the upper and lower expected fetal weights as parameters. In this case, the processing unit generates a range of ranking data conveying a range of levels of risk of shoulder dystocia associated to the obstetrics patient.

The following table illustrates a limited number of formats for expressing a ranking data element as a range of values. It will be appreciated that the ranking data element may be expressed in other suitable formats without detracting from the spirit of the invention.

| Sample Formats for Range of Ranking Data Elements | | | |
|---|---|---|---|
| Likelihood | Classification | Score | Colour Scheme |
| .10-.15 | Low risk | 100-120 | Green |
| .25-.30 | Medium risk to High risk | 150-160 | Yellow to Organe |
| .5-.7 | High risk | 190-200 | Orange |
| .8-.92 | High risk to Very high risk | 225-240 | Orange to Red |

In a specific example of implementation, processing unit 104 is operative for generating a false detection data element conveying a false positive detection rate associated to the ranking data element and a successful detection data element conveying a true positive detection rate associated to the ranking data element. In a specific implementation, the false detection data element and the successful detection data element are derived on the basis of a receiver operating curve associated to the predictive model used to generate the ranking data element. The receiver operating curve characterizes the effectiveness of the predictive model in its ability to estimate the level of risk of shoulder dystocia in a reference population. In a non-limiting implementation, the receiver operating curve is provided in the form of a mapping between various ranking data elements (or scores corresponding to various ranking data element) to associated false detection and successful detection data elements. The table below shows, in simplified form, a receiver operating curve for an arbitrary predictive model. It will be appreciated that the table below is shown for the purpose of illustration only and does not necessarily represent an actual receiver operating curve or actual scores or rankings.

| Ranking | False detection data element | Successful detection data element |
|---|---|---|
| 5 | 1% | 20% |
| 3 | 3% | 41% |
| 2 | 15% | 50% |
| 1 | 40% | 80% |

In the table above, we see that for an obstetrics patient having ranking of "1", with respect to a reference population, 80% of obstetrics patient where shoulder dystocia was present would be detected. However, 40% of patient who do not have shoulder dystocia would be falsely predicted to have shoulder dystocia. At the other end of the spectrum, we see that for an obstetrics patient having ranking of "5", with respect to a reference population, 20% of obstetrics patient where shoulder dystocia was present would be detected and only 1% of patient who would not have shoulder dystocia would be falsely predicted to have shoulder dystocia.

In a specific example of implementation, processing unit 104 is operative for deriving at least one recommendation data element associated to the ranking data element. The recommendation is derived on the basis of an intervention policy associated to shoulder dystocia. The policy is generally determined by a health care institution or professional association, usually a hospital, which determines a certain level of care. In a non-limiting implementation, the recommendation is derived at least in part on the basis of the ranking data element. In a non-limiting implementation, the policy data is provided in the form of a mapping between various ranking data elements (or scores corresponding to various ranking data element) and various recommendations. Alternatively, the policy data is provided in the form of a mapping between either one or both of a false detection data element and a successful detection data element and various recommendations. The table below shows, in simplified form, policy data for an arbitrary predictive model. It will be appreciated that the table below is shown for the purpose of illustration only and does not necessarily represent an actual intervention policy. In the table below, ranking data elements conveying risk levels associated to the various scores are also provided.

| Score | Ranking | Recommendation |
|---|---|---|
| 225 or higher | High risk | Intervention highly recommended |
| 175-225 | Medium risk | Intervention recommended |
| below 175 | Low risk | Intervention not recommended |

The policy data may be integral to processing unit 104 or may be received as an input via a user interface of the type described with reference to user interface 102.

Output 114 releases the data derived by processing unit 104 towards an output unit 106. The output unit 106 is coupled to the output 114 of apparatus 101 and is responsive to the released signal for displaying information conveyed by the ranking data element derived by processing unit 104 and optionally information conveyed by the recommendation data element, successful detection data element and the false detection data element. The output unit 106 may be in the form of any suitable device for conveying information to the physician or other health care professional. In a specific example of implementation, the output unit 106 can include a display screen, or in an alternative example of implementation, the output unit 106 can include a printing device for displaying the data in printed form.

The processing unit 104 in apparatus 101 is described in greater detail herein below with reference to FIG. 2.

As shown, the processing unit 104 includes a likelihood estimation module 210 and a display control module 240. Optionally, the processing unit 104 also includes a recommendation generation module 250. In use, the recommendation generation module 250 and display control module 240 make use of shoulder dystocia intervention policy data 220.

In the embodiment shown, the shoulder dystocia intervention policy data 220 is integrated as part of the processing unit 104. In an alternative embodiment (no shown in the figures), the policy data 220 may be provided to processing unit 104 through an input for receiving data signals conveying intervention policy data associated to shoulder dystocia. The input may be in communication with a data module or user interface device of a type similar to that described in connection with user interface 102 for receiving the intervention policy data associated to shoulder dystocia.

The likelihood estimation module 210 processes the set of information data elements received from the user interface 102 to generate a ranking data element 230 on the basis of a predictive model.

The display control module 240 receives the ranking data element 230 and generates control signals for causing output unit 106 to display information conveying the ranking data element.

The recommendation generation module 250 processes the ranking data element 230 on the basis of intervention policy data 220 to generate information conveying a recommendation.

Figure 4:
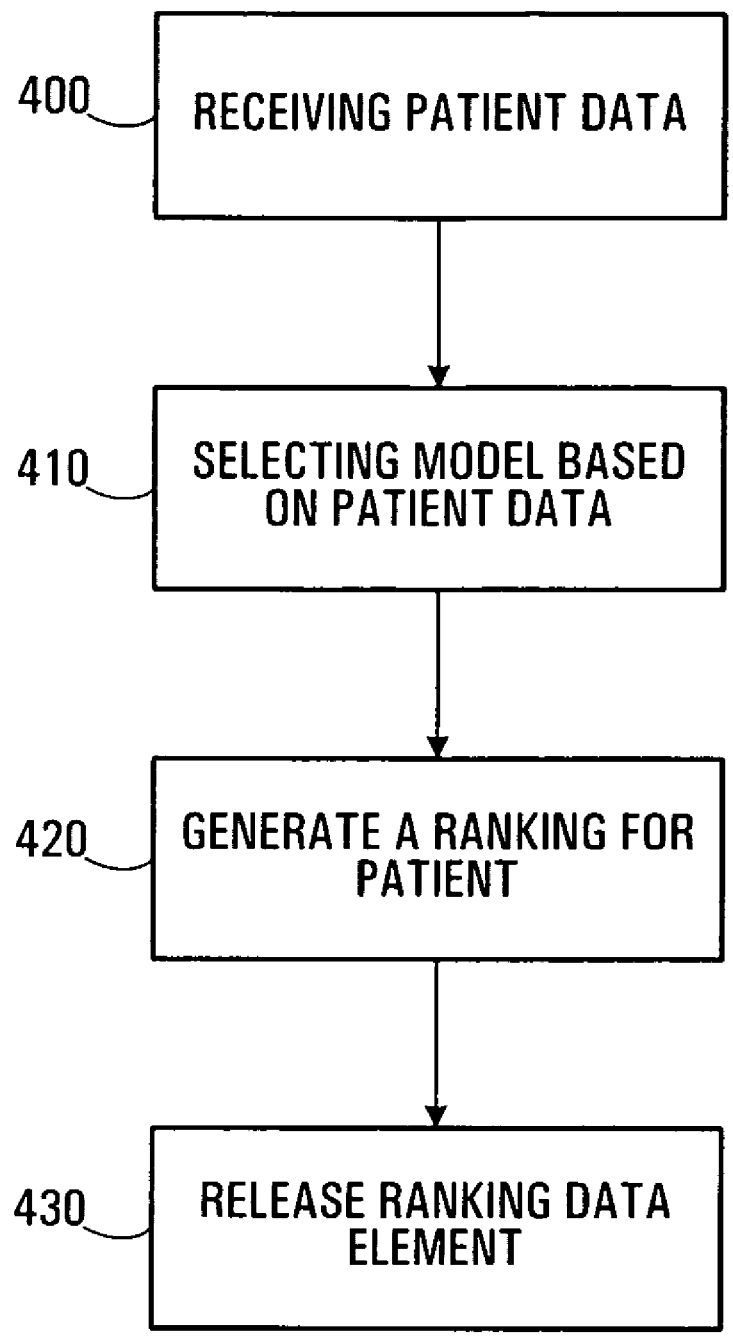
FIG. 4 a flow diagram of a method for estimating a level of risk of shoulder dystocia associated to an obstetrics patient in accordance with a specific example of implementation of the present invention.

The method for generating ranking data element 230 as implemented by likelihood estimation module 210 is described in greater detail herein below with reference to the flow chart shown in FIG. 4.

At step 400, the set of information data elements associated to an obstetrics patient is received. At step 410 (optional), the set of information data elements associated to an obstetrics patient is processed to select a predictive model from a set of predictive models. In a specific implementation, different predictive models are used for nulliparous and multiparous mothers. In such an implementation, the set of information data elements includes a previous vaginal birth indicator, which is used to select between the two models. Another example where multiple predictive models may be used is the diabetes status. It will be appreciated that different predictive models may be used for other factors without detracting from the spirit of the invention. Where a single predictive model is used by likelihood estimation module 210, step 410 may be omitted. In a specific example of implementation, the set of information data elements includes information derived from a maternal weight component, a maternal height component and a fetal weight component. The predictive model may include a factor having a ratio between the maternal weight component and the maternal height component. This factor may for example be a BMI (body mass index) factor. In a specific implementation, the predictive model includes a factor having the form [maternal BMI×fetal weight].

At step 420, the set of information data elements is processed by the predictive model to generate a ranking data element associated to the obstetrics patient. A false positive detection rate and a true positive detection rate associated to the ranking data element are also derived. In a non-limiting example of implementation, the false positive and true positive detection rates are derived on the basis of a receiver operating curve associated to the predictive model selected at step 410.

At step 430, the ranking data element is released by likelihood estimation module 210. A false detection data element conveying the false positive detection rate and a successful detection data element conveying the true positive detection rate are also released.

The recommendation generation module 250 receives the ranking data element, false detection data element and the successful detection data element and derives an intervention recommendation on the basis of the shoulder dystocia intervention policy data 220. The intervention recommendation is then released.

The display control module 240 is in communication with the likelihood estimation module 210 and the recommendation generation module 250. The display control module 240 generates a signal for causing a visual representation of the ranking data element and optionally the false detection data element, the successful detection data element and the intervention recommendation to be displayed to a user at output unit 106.

Figure 6:
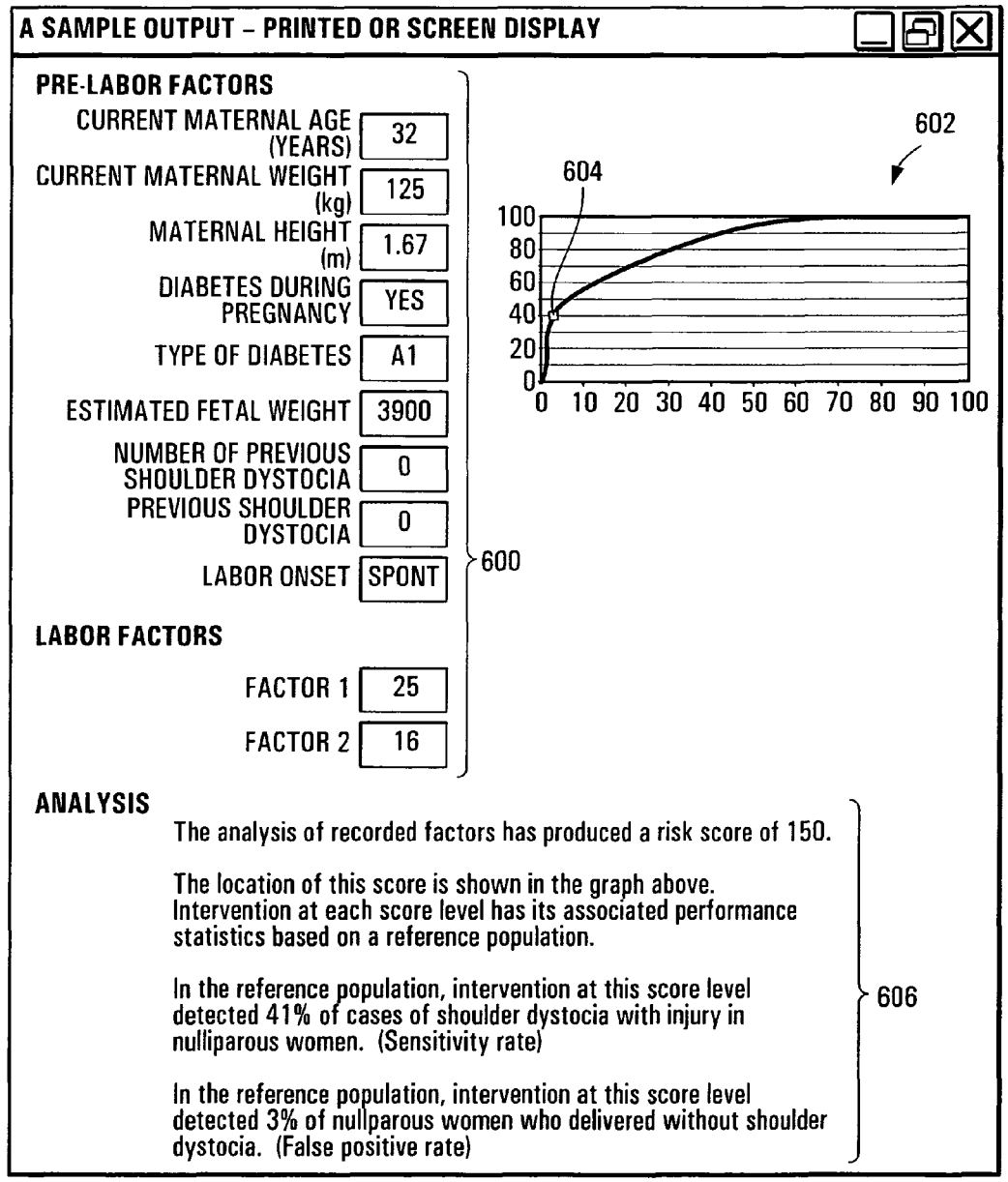
FIG. 6 shows a second non-limiting example of a visual representation of the data released by the processing unit shown in FIG. 1 in accordance with a specific example of implementation of the present invention.

FIGS. 5 and 6 show non-limiting examples of specific visual representations caused to be displayed by output unit 106.

The visual representation shown in FIG. 5 is in the form of a graphical window 500 that could be shown on the display screen of a computer, PDA or other suitable device. Alternatively, the visual representation shown in FIG. 5 may be in the form of a printout. The graphical window 500 includes a set of information sections 502, 504, 506 and 508. Information sections 502 and 504 are in the form of text boxes displaying a set of information data elements associated to the obstetrics patient. These text boxes include the information provided through user interface 102 (FIG. 1). Optionally, the text boxes include fields that may be edited by the user of the system 100 (FIG. 1) such as to modify or add information associated to the obstetrics patient. Information section 502 includes information element associated to the obstetrics patient which were obtained prior to labour onset. These pre-labour factors include, without being limited to, a maternal weight, a maternal height and an expected fetal weight. In this case the expected fetal weight is expressed as a range of fetal weights. The labour factors in information section 504 are marked "N/A" since the system is being used prior to labour onset. Information section 506 is a text box displaying the ranking data element. In this specific implementation, the range of fetal weights has resulted in a range of ranking data elements namely 8/10 to 9/10. Alternatively, information section 506 may be in the form of a graph depicting the ranking data element and its associated false detection data element and successful detection data element. Such a graph may be in the form of a receiver-operating curve for example. Information section 508 is a text box displaying an intervention recommendation associated to the ranking data element or range of ranking data elements.

The visual representation 601 shown in FIG. 6 may be shown on the display screen of a computer, PDA or other suitable device. Alternatively, the visual representation shown in FIG. 6 may be in the form of a paper printout. The paper printout may be particularly useful for example where the system 100 (FIG. 1) estimating a level of risk of shoulder dystocia associated to an obstetrics patient is part of a centralised testing service. A physician tracking an expectant mother may gather information and request that a likelihood of shoulder dystocia test be performed on the basis of that information. The paper printout, of the type shown in FIG. 6, or an electronic version thereof, may be provided to the physician as the result of such a test and be inserted into the expectant mother's file. The visual representation 601 shown in FIG. 6 includes a set of information sections 600, 602 and 606. Information section 600 displays data elements associated to the obstetrics patient including the information provided through user interface 102 (FIG. 1). Optionally, where the visual representation 601 is shown on a display screen, the information section 600 includes editable fields that may be modified by the user of the system 100 such as to modify or add information associated to the obstetrics patient. Information section 602 displays the ranking data element 604 and its associated false detection data element and successful detection data element. In the example depicted, the information is in the form of a graph showing a receiver-operating curve and the position of the ranking data element 604 on that curve.

Information section 606 includes information explaining the results shown in information section 602 and optionally an intervention recommendation (not shown) associated to the ranking data element.

It should be understood that window 500, as shown in FIG. 5, and sample output 601 shown in FIG. 6, are only examples of two specific visual representations of how the data derived by processing unit 104 (FIG. 1) can be displayed. It is within the scope of the invention for a visual representation to contain more or less information. For example, the output unit 106 could display the intervention recommendation associated to the ranking data element in a graphical format, or by using a coded colour scheme, or other display convention.

Another specific example of a visual representation caused to be displayed by output unit 106 will now be described with reference to FIGS. 17a to 17d. In this other specific example, a graphical user interface module 1700 is described through which patient information data elements may be entered and a corresponding level of risk of delivery with shoulder dystocia associated to an obstetrics patient may be conveyed.

The user interface module 1700 depicted in FIGS. 17a to 17d may be shown on the display screen of a computer, PDA or other suitable device. The user interface module 1700 may also be printed on a paper printout. The paper printout may be particularly useful for example where the system 100 (FIG. 1) estimating a level of risk of shoulder dystocia associated to an obstetrics patient is part of a centralised testing service. A physician tracking an expectant mother may gather information and request that a likelihood of shoulder dystocia test be performed on the basis of that information. The paper printout, of the type shown in FIGS. 17a to 17d, or an electronic version thereof, may be provided to the physician as the result of such a test and be inserted into the expectant mother's file.

FIGS. 17a to 17d depict a same graphical user interface where controls 1730 1732 1734 have been selectively enabled or disabled to depict various types of risk assessment information. The graphical user interface module 1700 will be described first with reference to FIG. 17a.

The graphical user interface module 1700 includes a set of user modifiable information fields 1702 for allowing a user to enter a set of patient information data elements associated to the obstetrics patient. The graphical user interface module 1700 also includes a control 1718 for allowing a user to cause the set of information data elements entered in the set of fields 1702 to be transmitted to a processing unit of the type described with reference to component 104 (FIGS. 1 and 2). The graphical user interface module 1700 also includes a result portion 1750 for displaying the patient risk data with reference to risk assessment information. Optionally (not shown in the figure), the graphical user interface module 1700 also includes field for providing patient identification information to identify the patient for which the test is being performed. This patient identification information can also be used to extract a stored version of a previously performed test for later review.

Each field in the set of user modifiable information fields 1702 may be of any suitable format including, but not limited to, editable text boxes, pull down menus (not shown in the figures) allowing for selecting an input from a list of possible inputs, selection buttons (see for example 1704 1706) and increment controls (not shown in the figures) to increase or decrease a numerical value in a text box. The user modifiable information fields in the set 1702 may be modified through user interface 102 (FIG. 1). In the specific example depicted, the set of user modifiable information fields 1702 includes a previous vaginal birth indicator (nulliparous or multiparous patient) 1704, a maternal diabetes indicator 1706, a maternal weight component 1708, gestational age 1710, a maternal height component 1712, a fetal weight component 1714 and an estimated range of fetal weights 1719. The previous vaginal birth indicator 1704 and the maternal diabetes indicator 1706 are both depicted in the form of a set of selection buttons. The fields for maternal weight component 1708, maternal height component 1712, fetal weight component 1714 and estimated range of fetal weights 1719 are each depicted as a combination of an editable text box and a set of selection buttons. Advantageously, the set of selection boxes for fields 1708 1712 1714 and 1719 allows the metrics used for the various information elements to be specified by the user.

Each of the user modifiable information fields in the set 1702 may be made compulsory or optional through the graphical user interface 1700 depending on the predictive model used to derive a level of risk of delivery with shoulder dystocia associated to an obstetrics patient. In addition, it will be readily apparent to the person skilled in the art in light of the present specification that the set of patient information data elements may include other fields for receiving suitable information data elements or may omit certain fields without detracting from the spirit of the invention.

Figure 2:
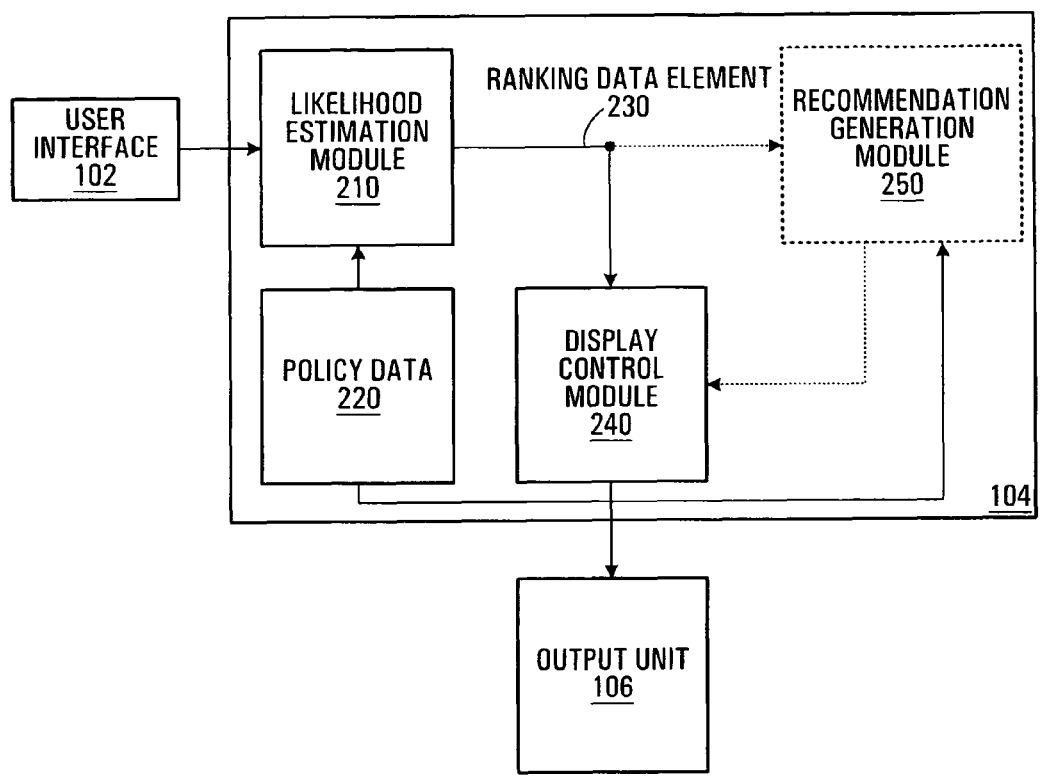
FIG. 2 shows a more detailed functional block diagram of the apparatus for estimating a level of risk of shoulder dystocia shown in FIG. 1 in accordance with a specific example of implementation of the present invention.

The control 1718 on the graphical user interface module 1700 is for allowing a user to cause the set of information data elements 1702 to be transmitted to a processing unit of the type described with reference to component 104 (FIGS. 1 and 2). The processing unit is adapted to derive patient risk data at least in part on the basis of the set of information data elements. The patient risk data conveys a level of risk of delivery with shoulder dystocia. In a specific implementation, the patient risk data is in the form of a ranking data element conveying a level of risk of delivery with shoulder dystocia associated to the obstetrics patient. The control 1718 may be actuated by a user through user interface 102 (FIG. 1) by using any suitable input device such as, for example, a mouse, keyboard, pointing device, speech recognition unit or touch sensitive screen. In the specific example depicted in FIG. 17a, the control is in the form of a button bearing the caption "CALCULATE NOW".

The result portion 1750 of the graphical user interface is for displaying the patient risk data with reference to risk assessment information.

The result portion 1750 includes a first graph 1762 conveying the level of risk of delivery with shoulder dystocia associated to the obstetrics patient with reference to a range of levels of risk. In the example depicted, the range of levels of risk is depicted by a horizontal axis representing a range of scores (or rankings) and the level of risk associated to the obstetrics patient is represented by a dotted line 1720 positioned along the corresponding score (or ranking). Optionally, a threshold level of risk 1726 is also depicted on the first graph 1762. In the example depicted, the threshold level of risk is depicted by a line positioned along a certain score (or ranking) corresponding to the threshold level of risk. In the example depicted, the threshold level of risk 1726 marks a boundary between scores (or rankings) considered to have a low level of risk of delivery with shoulder dystocia and scores (or rankings) considered to have a high level of risk of delivery with shoulder dystocia. The threshold level of risk 1726 may be a pre-determined value or may be a variable value. The threshold level of risk 1726 is typically established on the basis of a health care service provider's policy. Examples of the manner in which the threshold level of risk 1726 may be established will be described later on in the specification in particular with reference to FIGS. 7 and 10. Although a single threshold 1726 is depicted in graph 1762, it will be appreciated that multiple thresholds may also be used to mark, for example, boundaries between scores (or rankings) considered to have a low level of risk, moderate levels of risk and a high level of risk of delivery with shoulder dystocia.

Optionally, a sub-range of scores (or rankings) 1724 is also represented on the first graph 1762. The sub-range of scores (or rankings) 1724 is derived by using a range of estimated fetal weights defined by entry 1719. Advantageously, the sub-range of scores 1724 allows to account for errors in estimating the fetal weight.

Optionally still, in addition to the graph, or instead of the graph, an explanatory window 1722 is displayed for providing, in textual form, an indication of the level of risk of delivery with shoulder dystocia.

In situations where certain values provided in the user modifiable information fields in set 1702 are beyond allowable ranges for use of the predictive model, window 1722 may be used to convey an error message to the user. For example, in a case where an unusually low value was given for the maternal height (say 3'), the message in window 1722 may indicate:

"The allowable limits for maternal height range between 1.45 m (4'9") and 1.78 m (5'11"). The value entered is not valid for the present test."

Optionally still, the explanatory window 1722 may include a control 1780 for causing additional information to be displayed to the user. Such additional information may be displayed by expanding the explanatory window 1722 or, alternatively in an auxiliary window. Such additional information may include, for example, a more lengthy discussion about the predictive model used or about shoulder dystocia in general.

In the specific example depicted in FIG. 17a, the score (or ranking) 1720 associated to the obstetrics patient is below the threshold score (or ranking) 1726. This would indicate that the risks of delivery with shoulder dystocia for this patient are low. Furthermore, the sub-range of scores 1724 is also below the threshold score (or ranking) 1726. This would indicate that, even if the estimate of the fetal weight entered in field 1714 is inaccurate and may vary according to the range 1719, the risks of delivery with shoulder dystocia for this patient are also low.

The result portion 1750 also includes a second graph 1760 conveying patient risk data with reference to risk assessment information in graphical format. In the example depicted, the risk assessment information includes first information 1736 indicative of a reference range of levels of risk associated to women who delivered without shoulder dystocia. In the example depicted, the first information 1736 is depicted as a frequency distribution of the rankings associated to women who delivered without shoulder dystocia. The risk assessment information also includes second information 1740 indicative of a reference range of levels of risk associated to women who delivered with shoulder dystocia. In the example depicted, the second information 1740 is depicted as a frequency distribution of the rankings associated to women who delivered with shoulder dystocia with injury. The risk assessment information also includes third information 1726 conveying a threshold level of risk of delivery with shoulder dystocia. Optionally, different colors are used in the graph 1760 to display the first information 1736, second information 1740 and third information 1726 as well as the level of risk associated to the obstetrics patient 1720. Advantageously, the use of different colors allows for a greater ease in interpreted the information in graph 1760.

In a specific example of implementation, the graphical user interface module 1700 displays a second control 1730, a third control 1732 and a fourth control 1734 allowing a user to respectively cause the first information 1736, second information 1740 and third information 1726 to be selectively removed or added to/from the graph 1760.

FIG. 17a of the drawings depicts the graph 1760 with the second, third and fourth controls 1730 1732 1734 actuated to cause the first information 1736, second information 1740 and third information 1726 to be displayed.

FIG. 17b of the drawings depicts the graph 1760 with the second, third and fourth controls 1730 1732 1734 actuated to cause the second information 1740 and third information 1726 to be displayed but to cause the first information 1736 to be removed (or not displayed) on the graph 1760.

FIG. 17c of the drawings depicts the graph 1760 with the second, third and fourth controls 1730 1732 1734 actuated to cause the first information 1736 and third information 1726 to be displayed but to cause the second information 1740 to be removed (or not displayed) on the graph 1760.

FIG. 17d of the drawings depicts the graph 1760 with the second, third and fourth controls 1730 1732 1734 actuated to cause the third information 1726 to be displayed but to cause the first information 1736 and second information 1740 to be removed (or not displayed) on the graph 1760.

Advantageously, the second, third and fourth controls 1730 1732 1734 allow the clinical staff to select the risk assessment information against which level of risk 1720 associated to the obstetrics patient is displayed. As such, the clinical staff can remove information from the graph 1760 if it feels the graph 1760 is overly cluttered of may add information if it feels such information would be of use.

It will be readily apparent in light of the present description that combinations of actuation patterns for the second, third and fourth controls 1730 1732 1734 other than the ones depicted in the figures may be used for causing corresponding selected ones of the first information 1736, second information 1740 and third information 1726 to be displayed.

In addition, it will be readily apparent in light of the present description that, in certain alternative embodiments, first graph 1762 may be omitted and the information contained therein may be combined with that of second graph 1760.

It will be appreciated that although the specific example depicted in FIGS. 17a to 17d shows the graphical user interface module 1700 concurrently displaying the set of user modifiable information fields 1702 and the result portion 1750, alternative embodiments may display the set of user modifiable information fields 1702 and the result portion 1750 separately. Advantageously, by displaying the set of user modifiable information fields 1702 and the result portion 1750 concurrently, the clinical staff can more easily assess level of risk of delivery with shoulder dystocia shown in the result portion 1750, while taking into account the patient data in the information fields 1702. In addition, by displaying the set of user modifiable information fields 1702 and the result portion 1750 concurrently, mistakes in entering the data in fields 1702 can also be more easily detected and corrected.

Optionally, the result portion 1750 includes an editable field 1738 that may be modified by the user such as to add information associated to the obstetrics patient. This information may include for example additional observations made by the physician or other health care giver. Optionally still, the result portion 1750 includes an intervention recommendation field (not shown) for conveying recommendation data. In a non-limiting example of implementation, functionality is provided to allow the physician or other health care provider to enter information regarding the actual patient outcome in a standardised manner. FIG. 20 of the drawings show a specific example of implementation of user interface for allowing a health care practitioner to provide outcome information. Advantageously, the outcome information may be used in combination with the prediction information to generate correlation data conveying a level of accuracy of the model being used, to perform trend analysis and to compile information regarding use and/or rates of use of the testing system amongst others.

Optionally, the graphical user interface module 1700 includes controls for performing file management functions such as, but not limited to, saving results (control 1752), printing results (control 1754) and clearing the set of user modifiable information fields 1702 (control 1756).

Optionally, the graphical user interface module 1700 provides functionality for modifying the threshold level of risk 1726. The modification may be performed manually by the user of the system or may be modified on the basis of information provided by the user such as, for example, a hospital identifier or a location (country, province, city, etc . . . ), log-in information provided by the user, a desired false detection rate or any other suitable information.

Advantageously, by providing a threshold level that can be modified, different thresholds could be specified, for example, for different hospitals, for different geographical regions or for different individuals.

Figure 19:
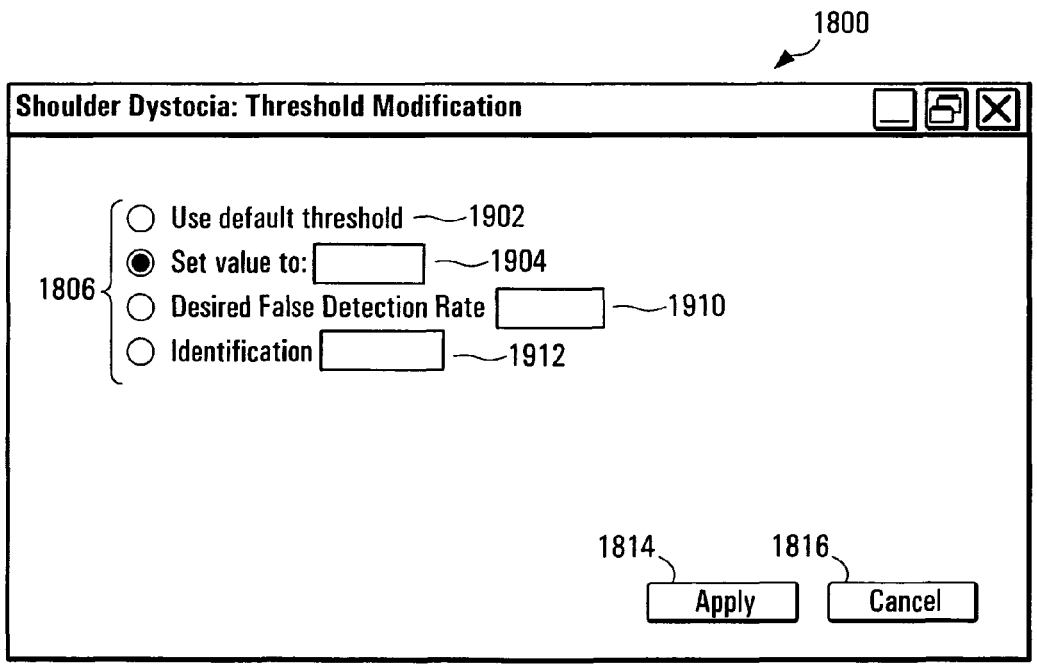
FIG. 19 shows a specific example of implementation of a user interface for modifying a threshold level of risk of delivery with shoulder dystocia in accordance with a non-limiting example of implementation of the invention.

In a first non-limiting example of implementation, user modifiable fields (not shown) are provided on the graphical user interface module 1700 for allowing a user to provide information to set a desired threshold level of risk. The user modifiable fields may include one or more of a hospital identifier field, a location field (country, province, city, etc . . . ), log-in information fields, a desired false detection rate field or any other suitable information field. It will be readily apparent that the user modifiable fields (not shown) for allowing a user to provide information to set a desired threshold level of risk need not be included as part graphical user interface module 1700 but may be included as a separate window. This separate window, can for example, be accessed through the graphical user interface module 1700 by providing a control (not shown) to that effect on the graphical user interface module 1700. This control (not shown) can be labelled, for example, "MODIFY THRESHOLD". A non-limiting visual representation of such a window 1900 is depicted in FIG. 19. In this specific non-limiting example, a set of choices 1906 is presented to the user to allow the latter to modify the threshold level. In this non-limiting example, the set of choices 1906 is mutually exclusive and is presented as a group of selection buttons only one of which may be actuated at a given time. The set of choices 1906 includes a first entry 1902 for setting the threshold to a default threshold value, a second entry 1904 for selecting a custom threshold value, a third entry 1906 for providing a desired false detection rate 1910 and a fourth entry for providing an identifier 1912. The identifier 1912 may be associated to the user or to a health care establishment, for example. The identifier 1912 provided is used to derive an associated threshold level. It will be appreciated that the set of choices 1906 may include additional suitable entries not shown in the figures such as location information (city, province, state, country etc . . . ) or any other type of suitable information for establishing a threshold value. It will be appreciated that the set of choices 1906 in alternative implementations may omit certain ones of the entries shown in FIG. 19 without detracting from the spirit of the invention. In the example depicted, controls 1914 1916 are provided in order to respectively apply or cancel the selections made in window 1900.

In a second non-limiting example of implementation, the graphical user interface module 1700 can only be accessed by authorised individuals and an access control mechanism is provided. Any suitable access control mechanism may be used. Such access control mechanisms are well known in the art and as such will not be described further here. A number of advantages may be had by controlling the access to the graphical user interface module 1700. For example, a fee may be charged to the users of the graphical user interface module 1700. The fee may, for example, be levied on a per use basis or on the basis of a subscription obtained for a pre-determined period of time. In addition, storage capabilities may be provided to the user for storing data associated to patients as well as the results of the computations performed through graphical user interface module 1700. By controlling the access to the graphical user interface module 1700, it is possible to provide confidential storage capabilities.

Figure 18:
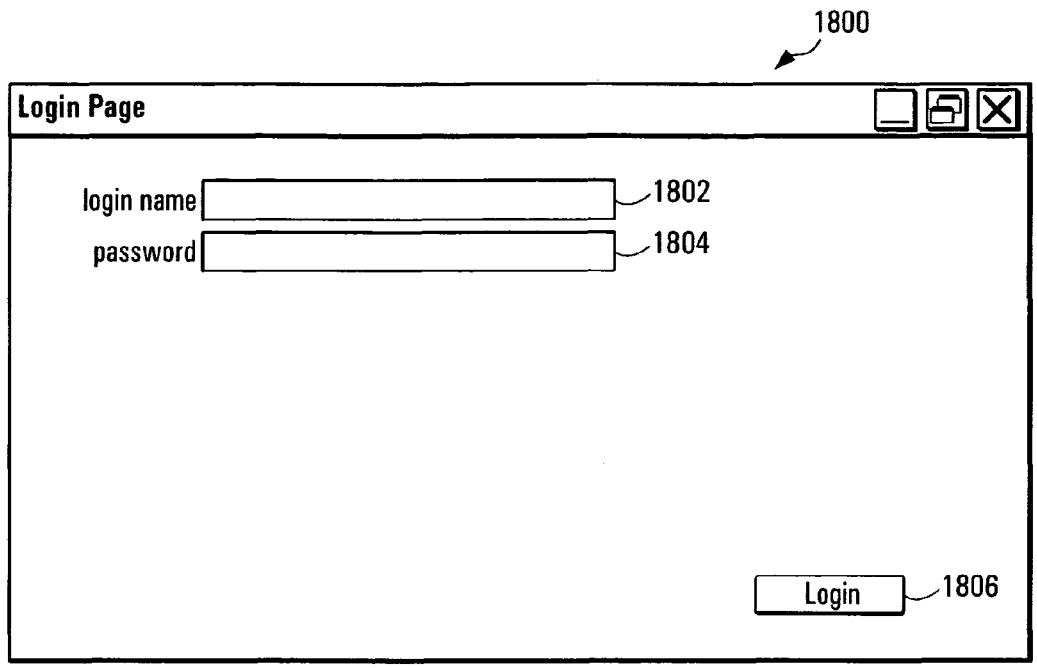
FIG. 18 shows a specific example of implementation of a login user interface in accordance with a non-limiting example of implementation of the invention.

In a non-limiting example of implementation, a login page 1800 of the type depicted in FIG. 18 is used. The login page 1800 includes a user identifier field (or login name field) 1802 and a password field 1804. In a typical interaction, when a user wishes to access the graphical user interface module 1700, he is first presented with login page 1800. The user enters the required data in the user identifier field (or login name field) 1802 and password field 1804 and then actuates control 1806. A log-in process is then initiated in accordance to any suitable well-known mechanism. The log-in process allows determining whether the user is allowed to gain access to the graphical user interface module 1700. The log-in process also allows determining the identity of the user (or the identity of a group to which the user belongs). The identity of the user can be associated to user preferences, including, but not limited to, a threshold level of risk. When the login-in process is completed, the user is given access to use the functionality of graphical user interface 1700.

Predictive Model Generation

The system 100 depicted in FIG. 1 makes use of a predictive model that combines a set of information data elements associated to an obstetrics patient to derive a score conveying a level of risk of shoulder dystocia. This predictive model is implemented by the likelihood estimation module 210 depicted in FIG. 2 of the drawings. The following portion of the present specification will describe the generation of a specific predictive model as an example. It will be readily apparent to the person skilled in the art of statistical analysis in light of the present specification that different predictive models may be used to derive a score conveying a level of risk of shoulder dystocia without detracting from the spirit of the invention.

In a specific implementation, the predictive model combines a BMI (Body Mass Index) associated to the mother and the fetal weight to derive a score.

Figure 8:
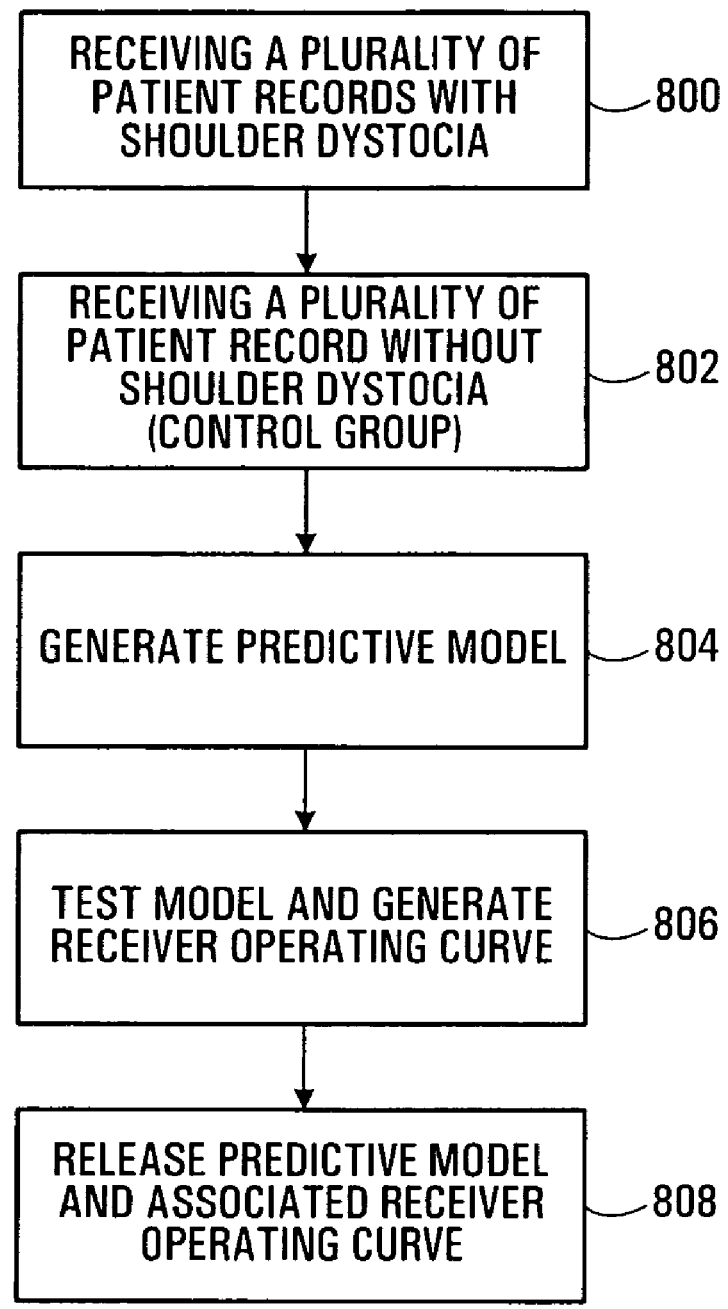
FIG. 8 shows a flow diagram of a process for generating a predictive model for estimating a level of risk of shoulder dystocia associated to an obstetrics patient in accordance with a specific example of implementation of the present invention.

FIG. 8 of the drawings shows a flow diagram of a specific example of implementation of a process for generating a predictive model for estimating a level of risk of shoulder dystocia associated to an obstetrics patient. The process depicted in FIG. 8 releases a predictive model that combines a set of information data elements associated to an obstetrics patient. In a specific implementation, the process also releases a receiver operating curve associated to the predictive model. The receiver operating curve includes data elements mapping scores conveying levels of risk of shoulder dystocia to corresponding false positive detection rates and successful true positive detection rates.

As depicted, at step 800 a database of patient records with shoulder dystocia is received, each record being associated to an obstetrics patient for which shoulder dystocia was observed. Preferably, the patient records received at step 800 include records where shoulder dystocia with neonatal injury was observed.

Figure 9:
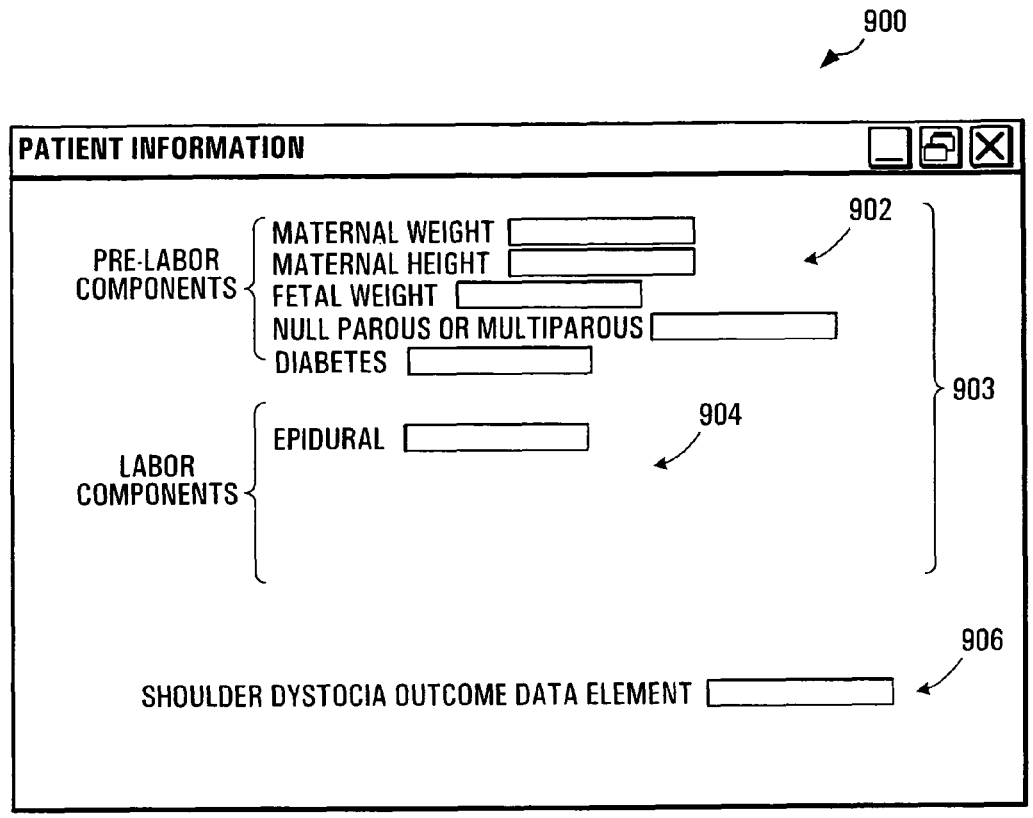
FIG. 9 shows a set of information data elements associated to an obstetrics patient in accordance with a non-limiting example of implementation of the present invention suitable for use in the process shown in FIG. 8.

For the purpose of illustration only, a sample record in the database of patient records received at step 800 is depicted in FIG. 9. Each record includes a set of patient information data elements 903 and a shoulder dystocia outcome data element 906. As shown, the set of patient data elements 903 includes pre-labour components including a maternal weight component, a maternal height component and a fetal weight component. Alternatively (not shown), the set of patient data elements includes a maternal Body Mass Index component and a fetal weight component. Optionally, the set of patient data elements 903 includes a previous vaginal birth indicator data element indicating whether the mother was nulliparous or multiparous. Optionally still, the set of patient data elements 903 includes labour components 904. It will be appreciated that the set of patient data elements 903 may include additional components without detracting from the spirit of the invention. The shoulder dystocia outcome data element 906 indicates whether shoulder dystocia was observed for the patient or whether shoulder dystocia was observed for that patient. In the case of the records in the database of patient records with shoulder dystocia, the shoulder dystocia outcome data element 906 indicates that shoulder dystocia was observed. In a non-limiting implementation, when shoulder dystocia was observed for a given patient, the shoulder dystocia outcome data element 906 may further indicate whether shoulder dystocia was present with neonatal injury or without neonatal injury. It will be appreciated that in order to generate a suitable model, a sufficient number of patient records with shoulder dystocia should be provided. It has been observed that improved performance has been obtained where the database of patient records with shoulder dystocia included records where the shoulder dystocia outcome data element 906 indicated that shoulder dystocia was present with neonatal injury.

At step 802, a control database including a plurality of records is received, each record being associated to an obstetrics patient where shoulder dystocia was not observed. The records in the control database are similar in format to the records in the database of patient records described in connection with FIG. 9. In the case of the records in the control database, the shoulder dystocia outcome data element 906 indicates that shoulder dystocia was not present. Preferably, in order to generate a model having a higher level of performance, the records received at step 800 and 802 should reflect the population in which the end system (of the type shown in FIG. 1) will be used. For example, the maternal weights and heights of the patients in the records received at steps 800 and 802 should be similar to those of the patients on which the system will be used. If the model is developed on records where the mothers were consistently overweight or obese, the model may not perform well in a population where the population does not have this characteristic and vice versa—a model developed on records where the mothers are of average weight and height may not perform well in a population where the mothers are frequently overweight.

In a specific non-limiting example of implementation, the database of patient records received at step 800 included a plurality of patient records for which the shoulder dystocia outcome data element 906 indicated that shoulder dystocia was present with neonatal injury. Each record was then matched one to one (1:1) based on parity, race, fetal birthweight and induction to a record in the control database received at step 802.

At step 804, a predictive model is generated. The model establishes a relationship between the set of patient data elements, a score and the shoulder dystocia outcome data element. In a non-limiting implementation, the mathematical model combines the set of patient data elements such as to derive a score. The score is then used to assign a ranking to the obstetrics patient. The ranking data element may be the score itself, a number, a likelihood, a risk level selected from a set of risk levels or any other format suitable for conveying a likelihood.

Different combinations of patient data elements in the set of patient data elements can be used. The combinations may be derived using heuristic techniques alone or using a combination of heuristic techniques and statistical tools.

In a specific implementation, a crude predictive model combining a maternal weight component, a maternal height component and a fetal weight component was tested having the form:

$$\text{SCORE} = \text{BMI} \times \text{fetal weight} \qquad \text{(Equation \#1)}$$

where BMI denotes the body mass index of the mother. The Body mass index (BMI) of the mother is a well-known metric derived on the basis of the maternal weight component and the maternal height component. The Body mass index (BMI) is a measure of body fat based on height and weight that applies to both adult men and women. It is a number that shows body weight adjusted for height. BMI can be calculated with simple math using inches and pounds, or meters and kilograms.

Body Mass Index can be calculated using pounds and inches with this equation:

$$BMI = \left( \frac{\text{Weight in Pounds}}{(\text{Height in inches}) \times (\text{Height in inches})} \right) \times 703$$

Body Mass Index can also be calculated using kilograms and meters (or centimeters):

$$BMI = \frac{\text{Weight in Kilograms}}{(\text{Height in Meters}) \times (\text{Height in Meters})} \quad \text{or}$$

$$BMI = \left( \frac{\text{Weight in Kilograms}}{(\text{Height in centimeters}) \times (\text{Height in centimeters})} \right) \times 10{,}000$$

It will be observed that terms 703 and 10000 in the above noted equations simply multiply the score by a constant value and therefore may be omitted entirely from the BMI.

Other more generalized forms for predictive models combining a maternal weight component, a maternal height component and a fetal weight component that could be used are the following:

$$\text{SCORE} = (\alpha \times \text{BMI})^m \times (\beta \times \text{fetal weight})^n \qquad \text{(Equation \#2)}$$

$$\text{SCORE} = \left[ \frac{(\alpha \times \text{maternal weight})^k}{(\delta \times \text{maternal height})^w} \right]^m \times (\beta \times \text{fetal weight})^n \qquad \text{(Equation \#3)}$$

Where α, β, δ, "k", "w", "m" and "n" are either whole numbers or ratios. Different predictive models may be generated for different combinations of α, β, δ, "k", "w", "m" and "n".

The relative performance of the different predictive models generated can then be compared using known statistical methods including for example receiver operating curves (ROC). The ROCs can be used to effect of a selection between several predictive models in order to choose a model yielding the best performance. The use of ROCs will be described later on in the specification.

It will be appreciated by the person skilled in the art of statistical analysis that more sophisticated predictive models could be used. Those more sophisticated model may include more complex mathematical functions and could be obtained using known statistical methods. In addition, although the above described predictive models includes a maternal weight component, a maternal height component and a fetal weight component, it is to be appreciated that additional suitable factors may be included in a predictive model without detracting from the spirit of the invention. Such factors include, without being limited to maternal age, maternal diabetes, multiparity, gestational age, previous vaginal birth, shoulder dystocia in previous pregnancies, induction of labour, epidural anesthesia, length of the first labour stage, the length of the labour second stage and intended operative vaginal delivery.

In a specific example of implementation, the predictive model generated includes a component associated to a previous vaginal birth indicator data element indicating whether the mother was nulliparous or multiparous. Alternatively, different predictive models are generated for nulliparous and multiparous mothers. Experimentation has shown that risk factors operate at different levels for nulliparous and multiparous women. By generating separate predictive models on the basis of whether the mothers had had previous births and generating separate predictive models for each group, predictive models having a higher level of performance can be obtained.

A specific example of a predictive models combining the above-described additional factors that could be used is the following:

| Variable | Coefficient |
|---|---|
| Constant | −12.4218 |
| Gestational Age (weeks) | −0.7046 |
| Parity(categorical 0 = nulliparity, 1 = multiparity) | −23.9382 |
| Gestational age * parity | 0.5808 |
| (BMI * Fetal weight (g))/1000 | 0.2232 |
| maternal weightKg/maternal height m | 0.0149 |
| (maternal weight Kg * Fetal weight(g)/ maternal height m)$^3$/1000 | 0.00008 |

The above table describes an equation for computing a score, where the items in the first column are the variable of the equations and the items in the second column represent the coefficients. The specific values of the coefficients presented in the above table were obtained through experimental data and as such may vary from one implementation to the other and should not be considered critical to the present invention. In a non-limiting implementation, the final score used is given by $e^x/(1+e^x)$ where x is the output of the formula described in the table above.

In a second specific example of implementation, different predictive models are generated for records with outcomes of shoulder dystocia with neonatal injury and for records with outcomes of shoulder dystocia without injury. The latter are medically and legally less significant and are not identified in a consistent fashion by clinicians. The models derived on records with outcomes of shoulder dystocia with neonatal injury have been found to be have a higher level of performance.

At step 806 the predictive model generated at step 804 is applied to a plurality of patient records. In a specific implementation, the predictive model is applied to the records in the database of patient records and the control group database received at steps 800 and 802.

Figure 14:
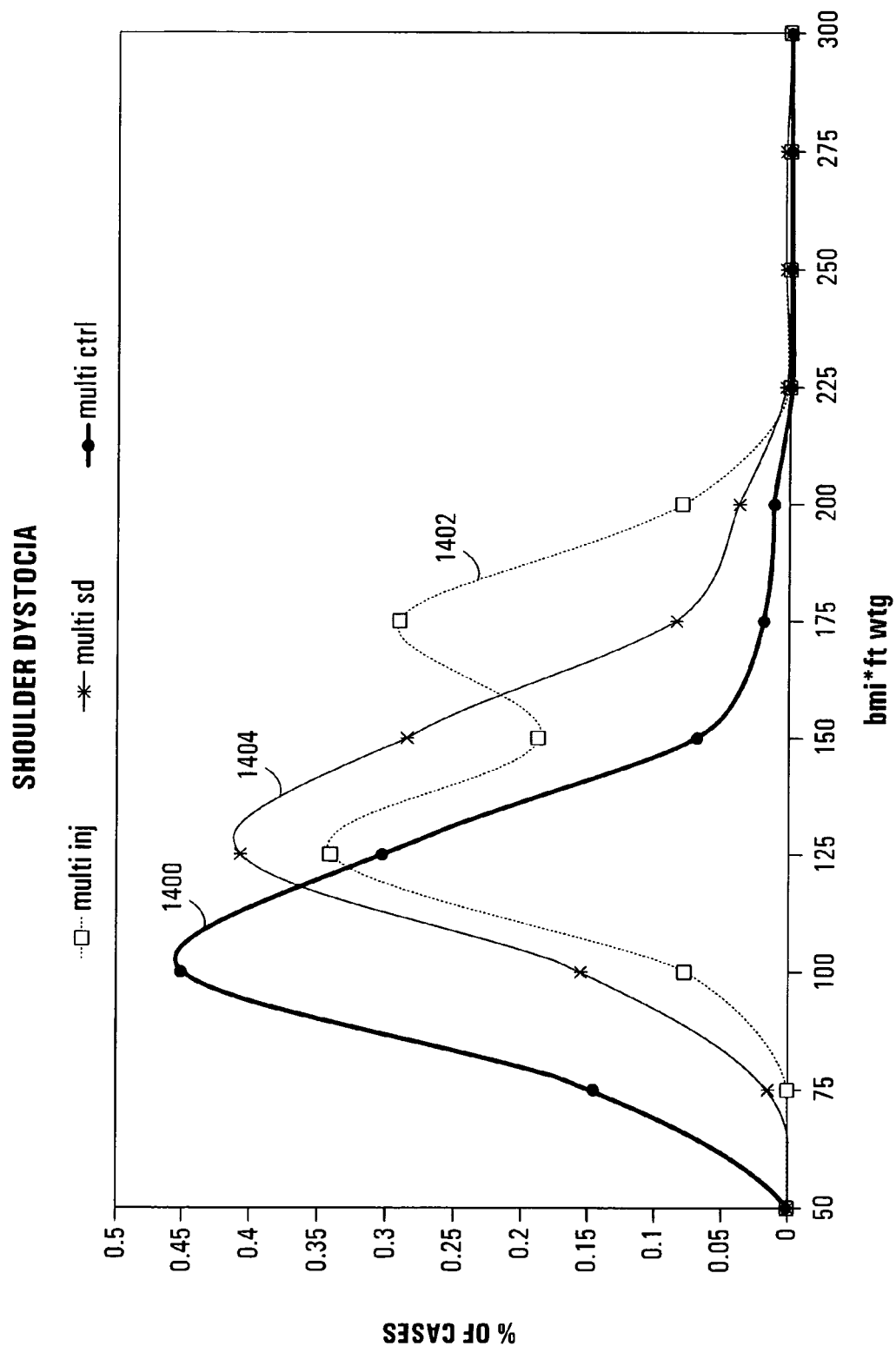
FIG. 14 is a frequency distribution of the scores for multiparous women generated by a predictive model applied to a reference population, the predictive model being suitable for use in the apparatus shown in FIG. 1 in accordance with a specific example of implementation of the present invention.

The predictive model is applied to each record in the database of patient records with identified shoulder dystocia and to the control database records to derive a score for each record. In a first experiment, the predictive model shown in equation 1 was applied to actual patient records from a control group, to a group of patient records having an identified shoulder dystocia with neonatal injury and to a group of patient records having an identified shoulder dystocia without neonatal injury. The patients in all three groups were multiparous women. FIG. 14 shows the frequency distribution of the scores derived on the basis of the predictive model shown in equation 1 plotted against the % of cases in the control group. This distribution is labeled 1400. FIG. 14 also shows the distribution of the scores plotted against the % of cases in the group of patient records for which shoulder dystocia without neonatal injury was observed. This distribution is labeled 1404. The figure also shows the distribution of the scores plotted against the % of cases in the group of patient records for which shoulder dystocia with neonatal injury was observed. This distribution is labeled 1402.

Figure 15:
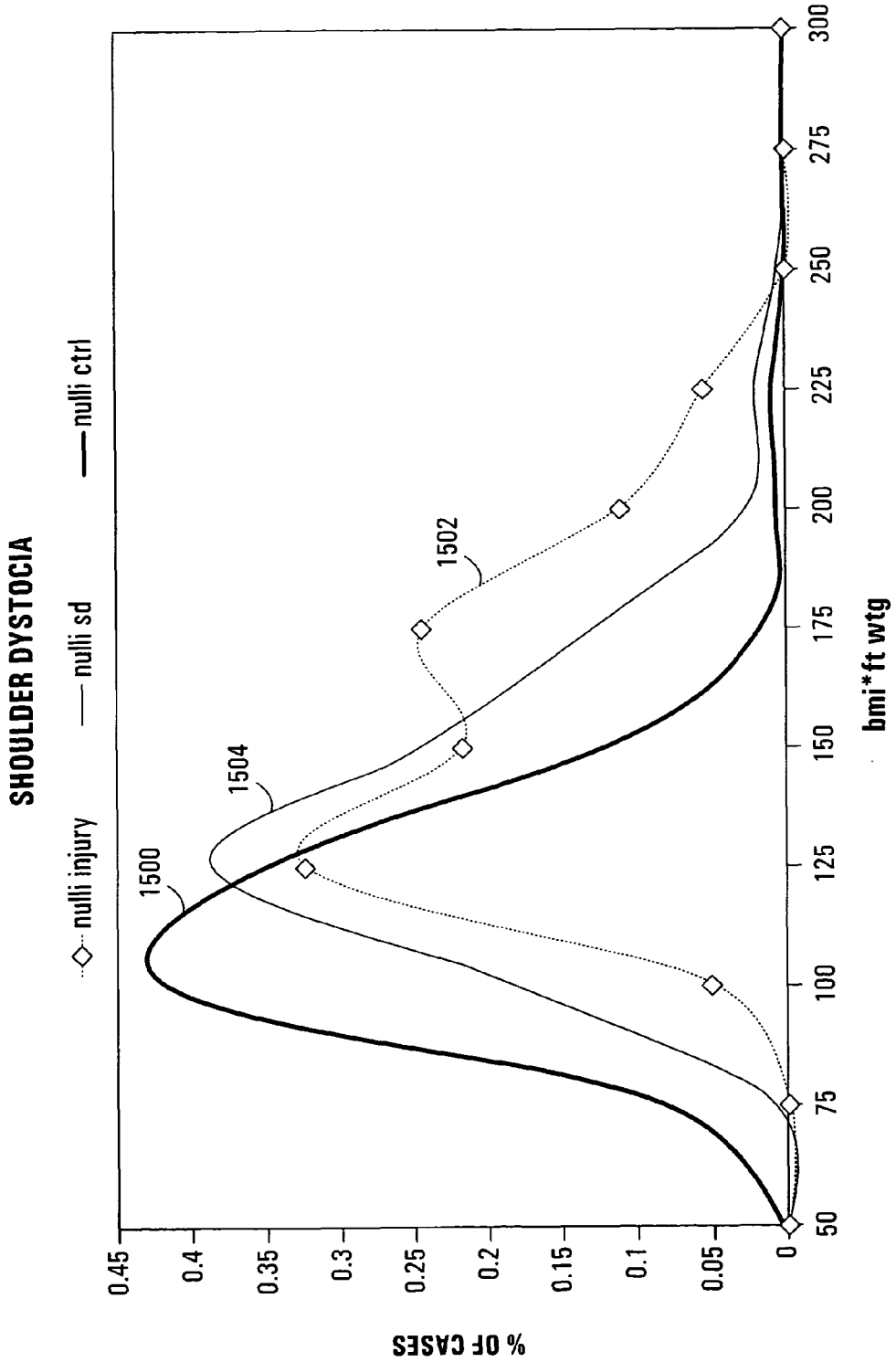
FIG. 15 is a frequency distribution of the scores for nulliparous women generated by a predictive model applied to a reference population, the predictive model being suitable for use in the apparatus shown in FIG. 1 in accordance with a specific example of implementation of the present invention.

In a second experiment, the predictive model shown in equation 1 was applied to actual patient records from a control group, to a group of patient records having an identified shoulder dystocia with neonatal injury and to a group of patient records having an identified shoulder dystocia without neonatal injury. The patients in all three groups were nulliparous women. FIG. 15 shows the frequency distribution of the scores derived on the basis of the predictive model shown in equation 1 plotted against the % of cases in the control group. This distribution is labeled 1500. The figure also shows the distribution of the scores plotted against the % of cases in the group of patient records for which shoulder dystocia without neonatal injury was observed. This distribution is labeled 1504. The figure also shows the distribution of the scores plotted against the % of cases in the group of patient records for which shoulder dystocia with neonatal injury was observed. This distribution is labeled 1502.

As can be observed from FIGS. 14 and 15, the scores are generally higher for the group of patient records for which shoulder dystocia without neonatal injury was observed than for the control group. It can also be observed that scores are generally higher for the group of patient records for which shoulder dystocia with neonatal injury was observed than for the group of patient records for which shoulder dystocia without injury was observed. From the graphs, it can be said that the greater the score, the greater the likelihood of shoulder dystocia. By selecting one or more threshold scores, various levels of risk of shoulder dystocia can be defined.

In a non-limiting implementation, at step 806 a receiver operating curve is generated. More specifically, for each score or range of scores, the true positive rate for the records in the database of records with shoulder dystocia received at step 800 and the false positive rate for the records in the control database is derived. The sets of true positive rates and false positive rates describe a receiver operating curve associated to the predictive model generated at step 804.

Figure 7:
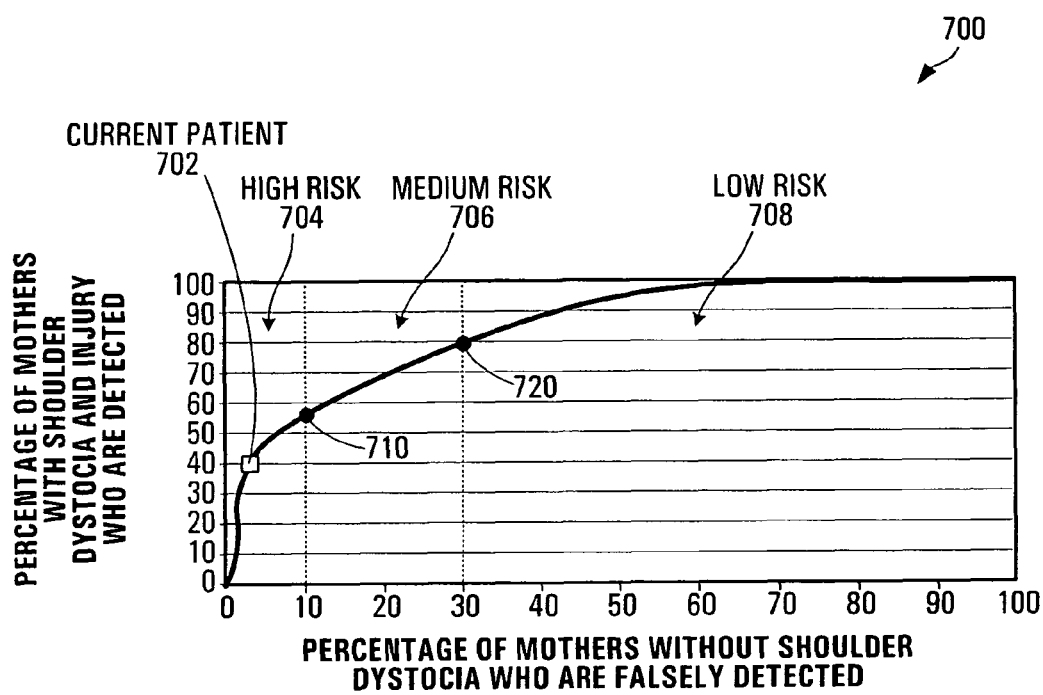
FIG. 7 shows a receiver operating curve associated to a predictive model suitable for use by the processing unit shown in FIG. 1 in accordance with a specific example of implementation of the present invention.

FIG. 7 of the drawings shows a generalised receiver operating curve 700 for a predictive model adapted for estimating a level of risk of shoulder dystocia associated to an obstetrics patient. The receiver operating curve 700 illustrates the effectiveness of the predictive model in estimating the level of risk in a reference population for various scores. The Y-axis shows the true positive rate or the percentage of women with shoulder dystocia and neonatal injury who are detected. The X-axis shows the false positive rate or the percentage of women without shoulder dystocia who are incorrectly detected. Each point on the curve corresponds to a particular level of score with its associated true positive and false positive rate. In FIG. 7, a certain obstetrics patient has been given a score which corresponds to point 702 on the receiver operating curve 700. This point 702 is associated to a true positive detection rate of 41% and a false positive detection rate of 3%. This means that in the reference population at point 702 the predictive model detected 41% of cases of shoulder dystocia (Sensitivity rate). This also means that in the reference population, the predictive model at point 702 detected 3% of women who delivered without shoulder dystocia (False positive rate). It will be appreciated that the numbers shown in FIG. 7 are used for the purpose of illustration only and not necessarily numbers indicative of the actual performance of the predictive model described in equation 1 above.

FIG. 7 also shows two threshold scores associated to reference numeral 710 and 720. This illustrates a manner in which an intervention policy for shoulder dystocia may be established. For example, at point 710, the predictive model detected 58% of cases of shoulder dystocia (Sensitivity rate) and detected 11% of women who delivered without shoulder dystocia (False positive rate). Any score falling to the left of point 710 has been classified as having a high risk 704 of shoulder dystocia. A corresponding recommendation for a high risk classification may then be established. Similarly, at point 720, the predictive model detected 80% of cases of shoulder dystocia (Sensitivity rate) and detected 30% of women who delivered without shoulder dystocia (False positive rate). Any score falling between point 710 and 720 has been classified as having a medium or moderate risk 706 of shoulder dystocia. A corresponding recommendation for a moderate risk classification may then be established. Finally, scores falling to the right of point 720 have been classified as having a low risk 708 of shoulder dystocia. A corresponding recommendation for a low risk classification may then be established. The table below illustrates a non-limiting example of a simplified shoulder dystocia intervention policy.

| False positive detection rate | Classification | Corresponding Threshold Score | Recommendation |
| --- | --- | --- | --- |
| 3% or less | High risk | 175 | Intervention highly recommended |
| 10% or less | Medium risk | 125 | Intervention recommended |
| over 10% | Low risk | 80 | Intervention not recommended |

In the above table, the classification is based on three classes namely: high risk, medium risk and low risk. It will be appreciated that more or fewer classes may be used to effect the classification, each class being associated to a respective level of risk. In another specific example, a classification based on a colour scheme is used where each level of risk is associated to a respective colour. The table below illustrates a non-limiting example of a shoulder dystocia intervention policy using a colour scheme:

| False positive detection rate | Classification | Recommendation |
| --- | --- | --- |
| 3% or less | RED | Intervention highly recommended |
| 8% or less | ORANGE | Intervention recommended |
| 10% or less | YELLOW | Intervention not usually recommended |
| over 10% | GREEN | Intervention not recommended |

Advantageously, the receiver operating curve associated with the predictive model allows demonstrating the discriminating performance of the predictive model and provides a health care institution with information upon which to set policies for intervention.

Figure 10:
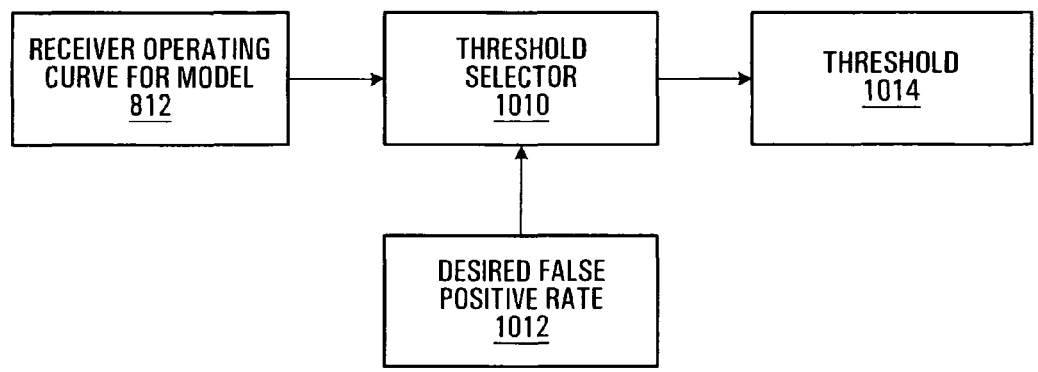
FIG. 10 shows a high-level functional block diagram of an apparatus for establishing an intervention policy for shoulder dystocia in accordance with a non-limiting example of implementation of the present invention.

FIG. 10 shows a block diagram of a device for selecting a threshold score on the basis of a desired false positive rate. More specifically, the device includes an input 812 for receiving the receiver operating curve for the predictive model, an input 1012 for receiving a desired false positive rate, or alternatively true positive rate (not shown), and a threshold selector unit 1010. The threshold selector unit processes the data received at inputs 812 and 1012 and releases the corresponding threshold score.

Figure 16:
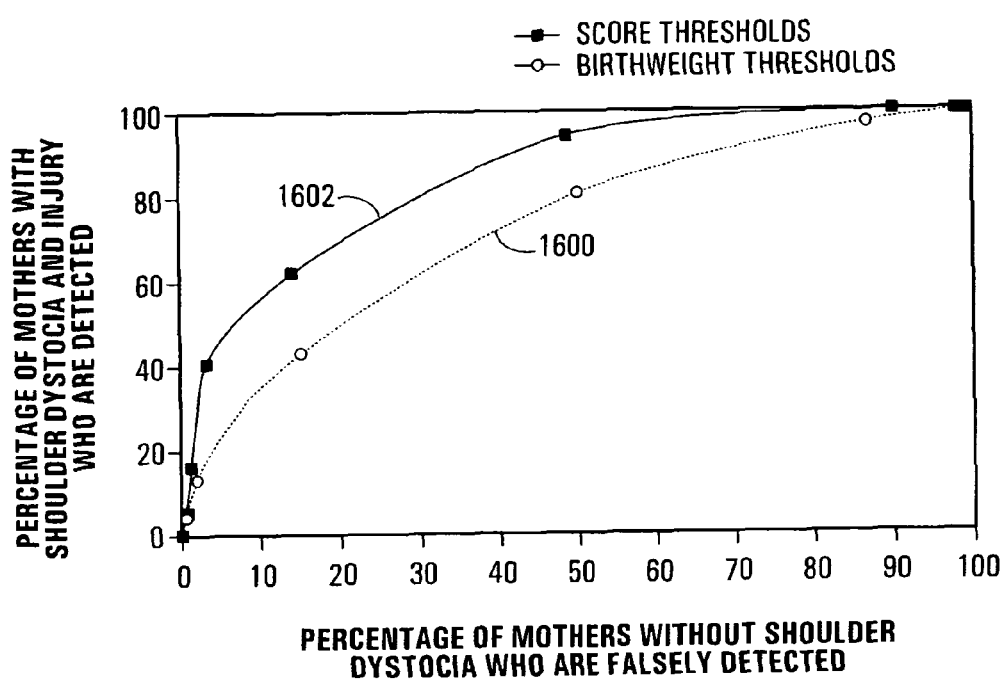
FIG. 16 shows two sample receiver operating curves, one for a predictive model using the fetal weight alone and the second for a predictive model using a combination of the maternal weight, maternal height and fetal weight.

The discriminating ability of a given predictive model can be measured and compared to other predictive models using the Receiver Operating Curve associated to each predictive model. In the basis of a reference population (control database+database of patient records with observed shoulder dystocia), it has been observed that the use of a predictive model which combines components of maternal weight, maternal height and fetal weight provides an improved performance in its ability to discriminate between cases with and without shoulder dystocia compared with the use of fetal weight alone. FIG. 16 shows two receiver operating curves 1600 and 1602. Receiving curve 1600 was generated on the basis of a predictive model using the fetal weight alone. Receiving curve 1602 was generated on the basis of a predictive model for nulliparous women using a combination of the maternal weight, maternal height and fetal weight in the form if BMI× fetal weight. Both predictive models were tested on the same set of records. As can be observed, for a same true positive value, the false positive is consistently lower for the predictive model using a combination of maternal weight, maternal height and fetal weight compared to the use of fetal weight alone for nulliparous women. Therefore, the use of a predictive model using a combination of maternal weight, maternal height and fetal weight in the form if BMI×fetal weight appears detect a higher percentage of babies with the condition of shoulder dystocia than the use of fetal weight alone for a same rate of false positive predictions for nulliparous mothers.

In implementations where multiple predictive models are used, as in the case for example of different models for multiparous mothers and nulliparous mothers, a receiver operating curve associated to each of the predictive models is generated at step 806.

The predictive model and the receiver operating curve associated to the predictive model are then released at step 808.

Non-Limiting Specific Practical Implementations

Those skilled in the art should appreciate that in some embodiments of the invention, all or part of the functionality for estimating a level of risk of shoulder dystocia associated to an obstetrics patient previously described herein with respect to the apparatus 101, may be implemented as preprogrammed hardware or firmware elements (e.g., application specific integrated circuits (ASICs), electrically erasable programmable read-only memories (EEPROMs), etc.), or other related components.

In other embodiments of the invention, all or part of the functionality previously described herein with respect to the apparatus 101 for estimating a level of risk of shoulder dystocia associated to an obstetrics patient may be implemented as software consisting of a series of instructions for execution by a computing unit. The series of instructions could be stored on a medium which is fixed, tangible and readable directly by the computing unit, (e.g., removable diskette, CD-ROM, ROM, PROM, EPROM, flash memory or fixed disk), or the instructions could be stored remotely but transmittable to the computing unit via a modem or other interface device (e.g., a communications adapter) connected to a network over a transmission medium. The transmission medium may be either a tangible medium (e.g., optical or analog communications lines) or a medium implemented using wireless techniques (e.g., microwave, infrared or other transmission schemes).

Figure 11:
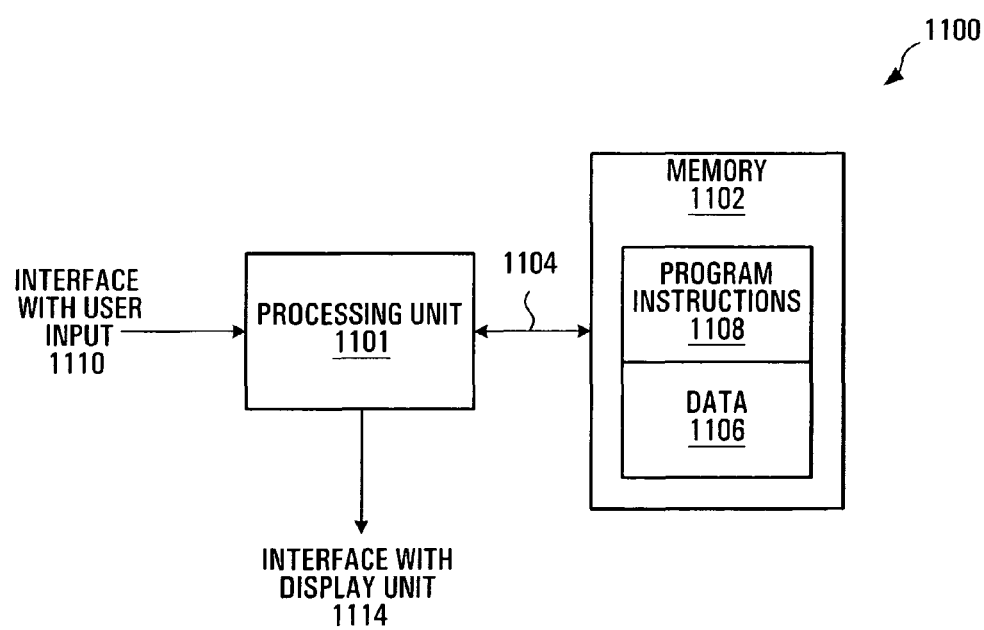
FIG. 11 shows a functional block diagram of an apparatus for estimating a level of risk of shoulder dystocia associated to an obstetrics patient in accordance with another specific example of implementation of the present invention.

The apparatus 101 for estimating a level of risk of shoulder dystocia associated to an obstetrics patient may be configured as a computing unit 1100 of the type depicted in FIG. 11, including a processing unit 1101 and a memory 1102 connected by a communication bus 1104. The memory 1102 includes data 1106 and program instructions 1108. The processing unit 1101 is adapted to process the data 1106 and the program instructions 1108 in order to implement the method described in the specification and depicted in the drawings. The computing unit 1100 may also comprise a number of interfaces 1110, and 1114 for receiving or sending data elements to external devices. For example, interface 1110 receives signals from user interface 102 as described with respect to FIG. 1, and as such is used for receiving data streams indicative of information data elements associated to an obstetrics patient. The processing unit 1101 is operative for processing the information data elements to derive a ranking data element conveying a level of risk of shoulder dystocia associated to the obstetrics patient. Interface 1114 is for releasing a signal conveying the ranking data element. The released signal is transmitted to output unit 106 (FIG. 1), such that output unit 106 may convey the ranking data derived by processing unit 1101 to a health care professional.

In a specific example of implementation, the memory 1102 includes a program element within the program instructions 1108, for execution by the computing unit 1100. Once the processing unit 1101 has derived the ranking data element conveying a level of risk of shoulder dystocia associated to the obstetrics patient, the program element is operative to process the data element so as to be able to convey information to a user on an output unit. As described above, in specific embodiment, the output unit 106 can include either one of a display screen or a paper printout.

Figure 12:
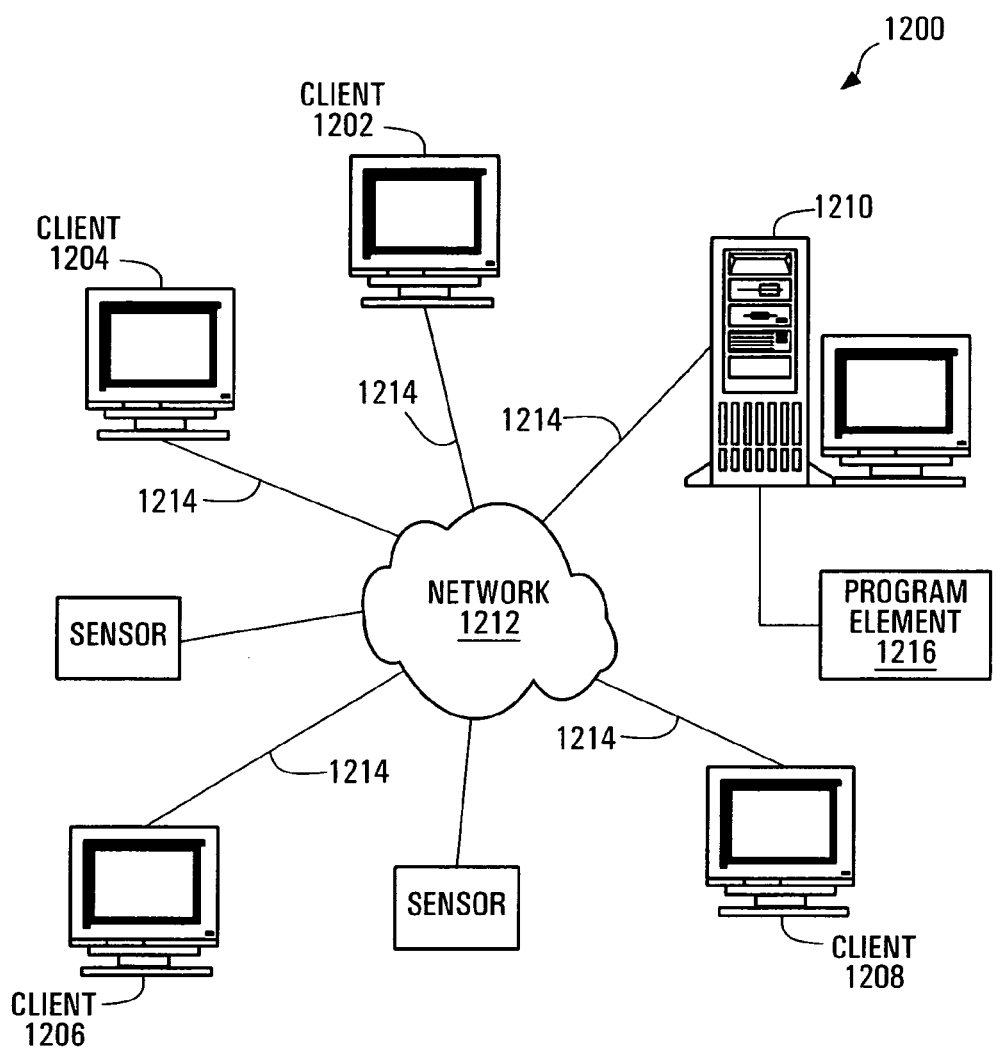
FIG. 12 shows a functional block diagram of a client-server system for estimating a level of risk of shoulder dystocia associated to an obstetrics patient in accordance with an alternative specific example of implementation of the present invention.

It will be appreciated that the system for estimating a level of risk of shoulder dystocia associated to an obstetrics patient may also be of a distributed nature where the set of information data elements associated to an obstetrics patient is collected at one location or more locations and transmitted over a network to a server unit implementing the method as described above. The server unit may then transmit a signal for causing an output unit to convey information to the user. The output unit may be located in the same location where the set of information data elements is being obtained or in the same location as the server unit or in yet another location. FIG. 12 illustrates a network-based client-server system 1200 for estimating a level of risk of shoulder dystocia associated to one or more obstetrics patients. The client-server system 1200 includes a plurality of client systems 1202, 1204, 1206 and 1208 connected to a server system 1210 through network 1212. The communication links 1214 between the client systems 1202, 1204, 1206 and 1208 and the server system 1210 can be metallic conductors, optical fibres or wireless, without departing from the spirit of the invention. The network 1212 may be any suitable network including but not limited to a global public network such as the Internet, a private network and a wireless network. The server 1210 may be adapted to process and issue signals concurrently using suitable methods known in the computer related arts.

The server system 1210 includes a program element 1216 for execution by a CPU. Program element 1216 implements similar functionality as program instructions 1108 (shown in FIG. 11) and includes the necessary networking functionality to allow the server system 1210 to communicate with the client systems 1202, 1204, 1206 and 1208 over network 1212. In a non-limiting example of implementation, program element 1216 includes a number of program element components, each program element components implementing a respective portion of the functionality of apparatus 101.

Figure 13:
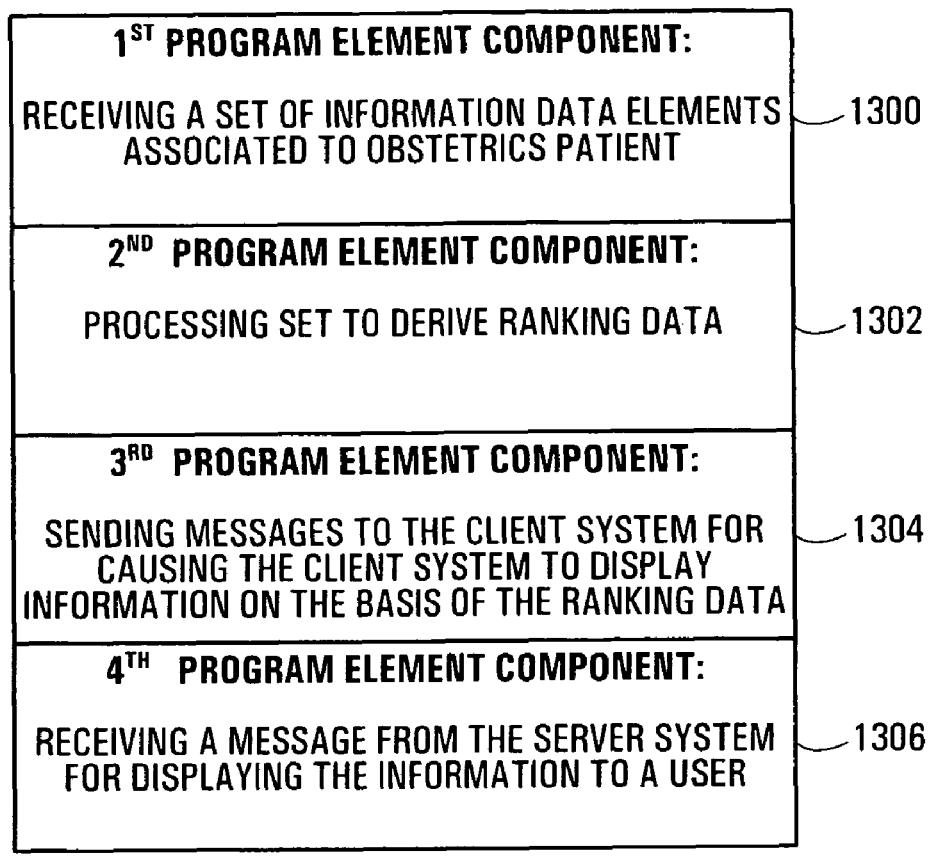
FIG. 13 is a conceptual representation of a computer readable storage medium storing a program element suitable for use in connection with the client-server system shown in FIG. 12 for estimating a level of risk of shoulder dystocia associated to an obstetrics patient in accordance with another specific example of implementation of the present invention.

FIG. 13 shows a non-limiting example of the architecture of an example of implementation of program element 1216 at the server system:

1. The first program element component 1300 is executed on server system 1210 and is for receiving a set of information data elements associated to an obstetrics patient. In a specific implementation, the set of information data elements includes information derived from a maternal weight component, a maternal height component and a fetal weight component.
2. The second program element component 1302 is executed on server system 1210 and is for processing the set of information data elements to derive a ranking data element associated to the obstetrics patient. The ranking data element conveys a level of risk of shoulder dystocia associated to the obstetrics patient.
3. The third program element component 1304 is executed on server system 1210 and is for sending messages to a client system (1202, 1204, 1206 or 1208) for causing the client system to display information on the basis of the data ranking data element.
4. The fourth program element component 1306 is executed on the client system and is for receiving a message from the server system 1210 for displaying the information to a user.

In a specific example of implementation, client systems 1202, 1204, 1206 and 1208 may include a program element suitable for implementing the graphical user interface depicted in FIGS. 17a to 17d. Alternatively, the program element to be executed by the client systems 1202, 1204, 1206 and 1208 is stored on server system 1210 can be accessed through network 1212 and downloaded onto the client systems for execution. In a non-limiting example of implementation, a client system accesses a web page stored on server system 1210 over the Internet or an Intranet which causes a graphical user interface of the type shown in FIGS. 17a to 17d to be displayed on the client system. Advantageously, the above-implemented graphical user interface allows a physician, or other health care service provider, to access a web page over a network (and preferably through a secure connection) and to enter various information regarding his obstetrics patient and to transmit this information to a server for processing. On the basis of this information, a representation of the level of risk of the patient for delivery with shoulder dystocia can then be displayed at the client system to the physician, or other health care service provider.

Those skilled in the art should further appreciate that the program instructions may be written in a number of programming languages for use with many computer architectures or operating systems. For example, some embodiments may be implemented in a procedural programming language (e.g., "C") or an object oriented programming language (e.g., "C++" or "JAVA").

Although the present invention has been described in considerable detail with reference to certain preferred embodiments thereof, variations and refinements are possible without departing from the spirit of the invention. Therefore, the scope of the invention should be limited only by the appended claims and their equivalents.

The invention claimed is:

1. A computer readable storage medium storing a program element suitable for execution by a processing unit, said program element implementing a graphical user interface module for displaying information conveying a level of risk of delivery with shoulder dystocia associated with an obstetrics patient, said graphical user interface module being configured for:
   a) displaying a set of user modifiable information fields for allowing a user to enter a set of patient information data elements associated with the obstetrics patient, said set of patient information data elements including:
      i. a maternal weight component;
      ii. a maternal height component; and
      iii. a fetal weight component;
   b) displaying a control allowing the user to cause said set of information data elements to be transmitted to a remote processing unit, and causing the remote processing unit to derive patient risk data at least in part based on said set of information data elements, the patient risk data conveying a level of risk of delivery with shoulder dystocia, said patient risk data being conditioned at least in part based on the fetal weight component and on a ratio between the maternal weight component and the maternal height component;
   c) receiving the patient risk data from the remote processing unit;
   d) displaying information derived from the patient risk data for viewing by the user.

2. A computer readable storage medium as defined in claim 1, wherein said patient risk data includes a ranking data element conveying a level of risk of delivery with shoulder dystocia associated with the obstetrics patient.

3. A computer readable storage medium as defined in claim 2, wherein said ranking data element is a likelihood score.

4. A computer readable storage medium as defined in claim 1, wherein said graphical user interface module is configured for displaying information derived from the patient risk data concurrently with risk assessment information, said risk assessment information conveying a reference range of levels of risk associated with women who delivered without shoulder dystocia.

5. A computer readable storage medium as defined in claim 4, wherein said reference range of levels of risk is a first reference range of levels of risk, said risk assessment information further conveying a second reference range of levels of risk associated with women who delivered with shoulder dystocia.

6. A computer readable storage medium as defined in claim 1, wherein said graphical user interface module is configured for displaying information derived from the patient risk data concurrently with risk assessment information, said risk assessment information conveying a reference range of levels of risk associated with women who delivered with shoulder dystocia.

7. A computer readable storage medium as defined in claim 1, wherein said graphical user interface module is configured for displaying information derived from the patient risk data in graphical format.

8. A computer readable storage medium as defined in claim 1, wherein said graphical user interface module is configured for displaying information derived from the patient risk data in textual format.

9. A computer readable storage medium as defined in claim 1, wherein said graphical user interface module is configured for displaying information derived from the patient risk data concurrently with risk assessment information, said risk assessment information further conveying a threshold level of risk.

10. A computer readable storage medium as defined in claim 1, wherein said control is a first control, said graphical user interface module being configured for displaying a second control allowing the user to cause a reference range of levels of risk associated with women who delivered without shoulder dystocia to be displayed.

11. A computer readable storage medium as defined in claim 1, wherein said control is a first control, said graphical user interface module being configured for displaying a second control allowing the user to cause a reference range of levels of risk associated with women who delivered with shoulder dystocia to be displayed.

12. A computer readable storage medium as defined in claim 1, wherein said graphical user interface module is configured for displaying a graph conveying risk assessment information including:
   (a) first information indicative of a reference range of levels of risk associated with women who delivered with shoulder dystocia;
   (b) second information indicative of a reference range of levels of risk associated with women who delivered without shoulder dystocia;
   (c) third information conveying a threshold level of risk of delivery with shoulder dystocia.

13. A computer readable storage medium as defined in claim 12, wherein said control is a first control, and wherein said graphical user interface module is configured for displaying a second control allowing the user to cause said first information to be removed from said graph conveying risk assessment information.

14. A computer readable storage medium as defined in claim 13, wherein said graphical user interface module is configured for displaying a third control allowing the user to cause said second information to be removed from said graph conveying risk assessment information.

15. A computer readable storage medium as defined in claim 14, wherein said graphical user interface module is configured for displaying a fourth control allowing the user to cause said third information to be removed from said graph conveying risk assessment information.

16. A computer readable storage medium as defined in claim 12, wherein the threshold level of risk of delivery with shoulder dystocia is pre-determined.

17. A computer readable storage medium as defined in claim 1, wherein the control allows the user to cause said set of information data elements to be transmitted to the remote processing unit by using an input device selected from the set consisting of a mouse, keyboard, pointing device, speech recognition unit and touch sensitive screen.

18. A computer readable storage medium as defined in claim 1, wherein said graphical user interface module is configured for displaying information derived from the patient risk data concurrently with risk assessment information, said risk assessment information conveying at least one recommendation data element associated with the obstetrics patient.

19. A computer readable storage medium as defined in claim 1, wherein said set of information data elements includes a previous vaginal birth indicator component.

20. A computer readable storage medium as defined in claim 1, wherein the fetal weight component is an estimated fetal weight component.

21. A computer readable storage medium as defined in claim 1, wherein the fetal weight component is a range of fetal weights.

22. An apparatus for implementing a user interface for displaying information conveying a level of risk of delivery with shoulder dystocia associated with an obstetrics patient, said apparatus comprising:
   a) an input device for allowing a user to enter information;
   b) a processing unit coupled to said input device, said processing unit being operative for implementing a graphical user interface module for displaying information conveying a level of risk of delivery with shoulder dystocia, said graphical user interface module being configured for:
      i. displaying a set of user modifiable information fields for allowing a user to enter using said input device a set of patient information data elements associated with the obstetrics patient, said set of patient information data elements including:
         1. a maternal weight component;
         2. a maternal height component; and
         3. a fetal weight component;
      ii. displaying a control allowing the user to cause said set of information data elements to be processed and causing patient risk data to be derived at least in part based on said set of information data elements, the patient risk data conveying a level of risk of delivery with shoulder dystocia, said patient risk data being conditioned at least in part based on the fetal weight component and on a ratio between the maternal weight component and the maternal height component;
      iii. displaying information derived from the patient risk;
   c) an output coupled to said processing unit, said output being suitable for releasing a signal for causing a display unit to display the graphical user interface module.

23. An apparatus as defined in claim 22, wherein said patient risk data includes a ranking data element conveying the level of risk of delivery with shoulder dystocia associated with the obstetrics patient.

24. An apparatus as defined in claim 23, wherein said ranking data element is a likelihood score.

25. An apparatus as defined in claim 22, wherein said graphical user interface module is configured for displaying information derived from the patient risk data concurrently with risk assessment information, said risk assessment information conveying a reference range of levels of risk associated with women who delivered without shoulder dystocia.

26. An apparatus as defined in claim 22, wherein said graphical user interface module is configured for displaying information derived from the patient risk data concurrently with risk assessment information, said risk assessment information conveying a threshold level of risk.

27. An apparatus as defined in claim 22, wherein said graphical user interface module is configured for displaying a graph conveying risk assessment information including:
   a) first information indicative of a reference range of levels of risk associated with women who delivered with shoulder dystocia;
   b) second information indicative of a reference range of levels of risk associated with women who delivered without shoulder dystocia;
   c) third information conveying a threshold level of risk of delivery with shoulder dystocia.

28. An apparatus as defined in claim 27, wherein said control is a first control, and wherein said graphical user interface module is configured for displaying a second control allowing the user to cause said first information to be removed from said graph conveying risk assessment information.

29. An apparatus as defined in claim 28, wherein said graphical user interface module is configured for displaying a third control allowing the user to cause said second information to be removed from said graph conveying risk assessment information.

30. An apparatus as defined in claim 29, wherein said graphical user interface module is configured for displaying a fourth control allowing the user to cause said third information to be removed from said graph conveying risk assessment information.

31. An apparatus as defined in claim 27, wherein the threshold level of risk of delivery with shoulder dystocia is predetermined.

32. An apparatus as defined in claim 22, wherein the control allows the user to cause said set of information data elements to be processed by using an input device selected from the set consisting of a mouse, keyboard, pointing device, speech recognition unit and touch sensitive screen.

33. An apparatus as defined in claim 22, wherein said set information data elements includes a previous vaginal birth indicator component.

34. A method suitable to be implemented on a general purpose computing unit for displaying information conveying a level of risk of delivery with shoulder dystocia associated with an obstetrics patient, said method comprising:
   a) displaying on a display unit associated with the general purpose computing unit a set of user modifiable information fields for allowing a user to provide a set of patient information data elements associated with the obstetrics patient, said set of patient information data elements including:
      i. a maternal weight component;
      ii. a maternal height component: and
      iii. a fetal weight component;
   b) displaying a control on the display unit allowing the user to cause said set of information data elements to be transmitted to a remote processing unit, and causing the remote processing unit to derive patient risk data at least in part based on said set of information data elements, the patient risk data conveying a level of risk of delivery with shoulder dystocia, said patient risk data being conditioned at least in part based on the fetal weight component and on a ratio between the maternal weight component and the maternal height component;
   c) displaying information derived from the patient risk data for viewing by the user.

35. A method suitable to be implemented on a general purpose computing unit for estimating a level of risk of delivery with shoulder dystocia associated with an obstetrics patient, said method comprising:

a) receiving at an input of the general purpose computing unit a set of information data elements associated with the obstetrics patient, the set of patient information data elements including information derived from:
   i. a maternal weight component;
   ii. a maternal height component; and
   iii. a fetal weight component;
b) transmitting said set of patient information data elements to a remote processing unit, and causing the remote processing unit to derive a ranking data element associated with the obstetrics patient, said ranking data element conveying a level of risk of delivery with shoulder dystocia, said ranking data element being conditioned at least in part based on the fetal weight component and on a ratio between the maternal weight component and the maternal height component;
c) receiving at the general purpose computing unit a signal conveying said ranking data element;
d) causing information derived from said ranking data element to be conveyed on a display unit in communication with the general purpose computing unit to convey a level of risk of delivery with shoulder dystocia associated with the obstetrics patient.

36. A method as defined in claim 35, wherein said ranking data element is indicative of a likelihood score.

37. A method as defined in claim 35, wherein said ranking data element is indicative of a risk level selected from a set of risk levels.

38. A method as defined in claim 35, wherein said method comprising receiving at the general purpose computing unit a signal conveying at least one recommendation data element associated with the obstetrics patient.

39. A method as defined in claim 35, wherein said set of patient information data elements includes a previous vaginal birth indicator data element.

40. A method as defined in claim 35, wherein the fetal weight component is an estimated fetal weight component.

41. A method as defined in claim 35, wherein the fetal weight component is a range of fetal weights.

42. An apparatus for implementing a user interface for displaying information conveying a level of risk of delivery with shoulder dystocia associated with an obstetrics patient, said apparatus comprising:
a) input means for allowing a user to enter information;
b) means for implementing a graphical user interface module for displaying information conveying a level of risk of delivery with shoulder dystocia, said graphical user interface module being configured for:
   i. displaying a set of user modifiable information fields for allowing a user using said input means to enter the set of patient information data elements associated with the obstetrics patient, said set of patient information data elements including:
      1. a maternal weight component;
      2. a maternal height component; and
      3. a fetal weight component;
   ii. displaying a control allowing the user to cause said set of information data elements to be processed and causing patient risk data to be derived at least in part based on said set of information data elements, the patient risk data conveying a level of risk of delivery with shoulder dystocia, said patient risk data being conditioned at least in part based on the fetal weight component and on a ratio between the maternal weight component and the maternal height component;
   iii. displaying information derived from the patient risk data;
c) means for releasing a signal for causing a display unit to display the graphical user interface module.

43. A computer readable storage medium storing a program element suitable for execution by a processing unit, said program element implementing a graphical user interface module for displaying information conveying a level of risk of delivery with shoulder dystocia associated with an obstetrics patient, said graphical user interface module being configured for:
a) displaying a set of user modifiable information fields for allowing a user to enter a set of patient information data elements associated with the obstetrics patient;
b) displaying a control allowing the user to cause said set of information data elements to be transmitted to a remote processing unit, and causing the remote processing unit to derive patient risk data at least in part based on said set of information data elements, the patient risk data conveying a level of risk of delivery with shoulder dystocia;
c) receiving the patient risk data from the remote processing unit;
d) displaying information derived from the patient risk data along with risk assessment information, said risk assessment information conveying a reference range of levels of risk associated with women who delivered without shoulder dystocia.

44. A computer readable storage medium as defined in claim 43, wherein said reference range of levels of risk is a first reference range of levels of risk, said risk assessment information further conveying a second reference range of levels of risk associated with women who delivered with shoulder dystocia.

45. A computer readable storage medium as defined in claim 43, wherein said control is a first control and wherein said reference range of levels of risk is a first reference range of levels of risk, said graphical user interface module being configured for displaying a second control allowing the user to cause a second reference range of levels of risk associated with women who delivered with shoulder dystocia to be displayed.

* * * * *